(12) United States Patent
Alihodzic et al.

(10) Patent No.: US 7,262,172 B2
(45) Date of Patent: Aug. 28, 2007

(54) MACROLIDES

(75) Inventors: Suleman Alihodzic, Zagreb (HR); Andrea Berdik, Zagreb (HR); Francesca Cardullo, Verona (IT); Antun Hutinec, Zagreb (HR); Gorjana Lazarevski, Zagreb (HR); Sergio Lociuro, Verona (IT); Zorica Marusic-Istuk, Zagreb (HR); Stjepan Mutak, Zagreb (HR); Alfonso Pozzan, Verona (IT); Marko Derek, Zagreb (HR)

(73) Assignees: Glaxo Group Limited, Greenford, Middlesex (GB); GlaxoSmithKline istrazivacki center Zagret d.o.o., Zagreb (HR)

( * ) Notice: Subject to any disclaimer, the term of this patent is extended or adjusted under 35 U.S.C. 154(b) by 0 days.

(21) Appl. No.: 10/399,426

(22) PCT Filed: Oct. 19, 2001

(86) PCT No.: PCT/IB01/02167

§ 371 (c)(1),
(2), (4) Date: Feb. 25, 2004

(87) PCT Pub. No.: WO02/32917

PCT Pub. Date: Apr. 25, 2002

(65) Prior Publication Data

US 2004/0254124 A1    Dec. 16, 2004

(30) Foreign Application Priority Data

Oct. 19, 2000  (GB) ................... 0025688.3

(51) Int. Cl.
*A61K 31/70* (2006.01)
*C07H 17/08* (2006.01)

(52) U.S. Cl. .......................... 514/29; 536/7.4
(58) Field of Classification Search ............. 536/7.4; 514/29

See application file for complete search history.

(56) References Cited

U.S. PATENT DOCUMENTS 6,110,965 A    8/2000  Kelneric et al.
6,593,360 B1 *  7/2003  Lazarevski .............. 514/460

FOREIGN PATENT DOCUMENTS

| EP | 0 508 699 A | 10/1992 |
| WO | WO99/12542 | 3/1999 |
| WO | WO 00/63223 | 10/2000 |

* cited by examiner

*Primary Examiner*—Elli Peselev
(74) *Attorney, Agent, or Firm*—Laura K. Madden; Loretta J. Sauermelch; Mary E. McCarthy

(57) ABSTRACT

The invention relates to novel semi-synthetic macrolides of formula (I) having antibacterial activity. More particularly this invention relates to derivatives of 8a-aza-8a-homoerythromycin A, to processes for their preparation, to compositions containing them and to their use in medicine (I)

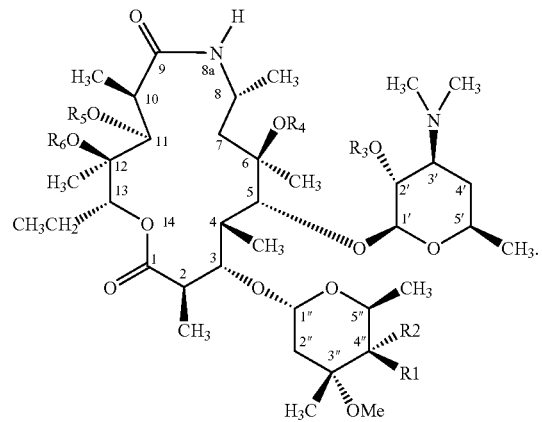

6 Claims, No Drawings

MACROLIDES

The present invention relates to novel semi-synthetic macrolides having antibacterial activity. More particularly this invention relates to derivatives of 8a-aza-8a-homoerythromycin A, to processes for their preparation, to compositions containing them and to their use in medicine.

8a-aza-8a-homoerythromycin A is a known 15 membered macrolide having the following formula (A)

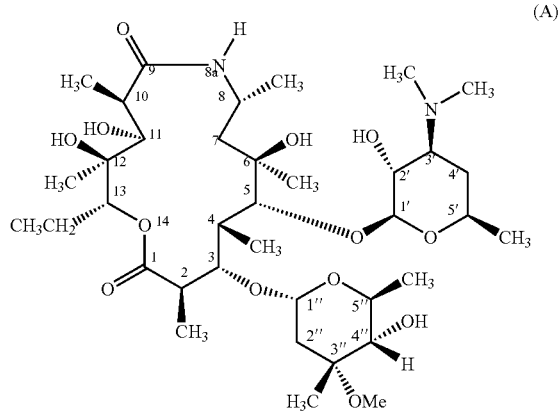

EP 0508699 inter alia generically discloses 8a-aza-8a-homoerythromycin A derivatives modified at the 4" position of the macrolide ring having antibacterial activity.

WO 99/12542 inter alia generically discloses 8a-aza-8a-homoerythromycin A derivatives modified at the 4" position as useful in the treatment or prevention of bacterial respiratory or enteric infections in a livestock animal.

WO 99/51616 describes the 6-O-methyl-8a-aza-8a-homoerythromycin A having antibacterial activity.

WO 00/63223 describes 3-decladinosyl-6-O-methyl-8a-aza-8a-homoerythromycin A derivatives modified at the 3 position of the macrolide ring having antibacterial activity.

We have now find novel derivatives of 8a-aza-8a-homoerythromycin A having antibacterial activity.

Thus, the present invention provides compounds of general formula (I)

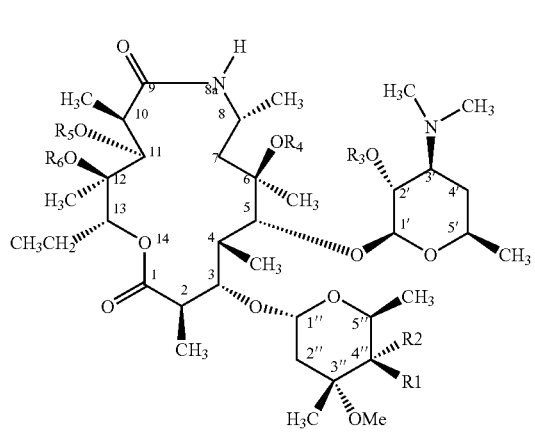

wherein
$R_1$ is hydrogen or together with $R_2$ is oxo;

$R_2$ represents hydroxy, $OC(O)XR_7$, $OC(O)NHXR_7$ or $R_2$ together with $R_1$ is an oxo group;
$R_3$ is hydrogen or a hydroxyl protecting group;
$R_4$ is hydrogen or $XR_7$;
$R_5$ is hydrogen, $XR_7$, $C(O)XR_7$ or $C(O)NHXR_7$;
$R_6$ is hydrogen or $R_5$ and $R_6$ taken together with the intervening atoms form a cyclic carbonate having the following structure

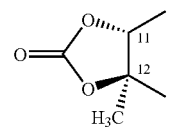

$R_7$ is selected from:
hydrogen,
optionally substituted phenyl,
optionally substituted phenoxy,
$C_{3-7}$ cycloalkyl,
optionally substituted 9 to 10 membered fused bicyclic carbocyclic,
optionally substituted 5 or 6 membered heteroaryl in which the 5-membered heteroaryl contains 1 or 2 heteroatoms selected from oxygen, sulphur or nitrogen and the 6-membered heteroaryl group contains 1 or 2 nitrogen atoms,
5-6 membered heterocyclic,
or
$R_7$ represents optionally substituted fused bicyclic heteroaryl containing 9 or 10 ring members having at least one heteroatom selected from oxygen, sulphur and nitrogen;
X is selected from:
a bond, $C_{1-12}$ alkylene (optionally substituted by one or two groups selected from a $C_{1-4}$ alkoxy, a halogen, a hydroxy or by a $NR_8R_9$), $C_{2-12}$ alkenyl (optionally substituted by one or two groups selected from a $C_{1-4}$ alkoxy, halogen, hydroxy or by $NR_8R_9$ group) or X represents a group $(CH_2)pY(CH_2)q$ wherein Y is C(O), O, S(O)n or $NR_8$;
$R_8$ and $R_9$ independently represent hydrogen or $C_{1-4}$ alkyl optionally substituted by 1 or 2 groups selected from:
phenyl, optionally substituted by $C_{1-4}$ alkoxy or nitro,
5-membered heteroaryl containing 1 or 2 heteroatoms selected from oxygen,
sulphur or nitrogen,
hydroxy,
oxo,
carboxy
or
$R_8$ and $R_9$ independently represent a phenyl optionally substituted by one or two $C_{1-4}$ alkyl, or a nitrogen protecting group;
n is 0 or an integer from 1 to 2;
p is an integer from 1 to 12; q is 0 or an integer from 1 to 11 with the proviso that the sum of p and q is an integer from 1 to 12; provided that
i) when $R_2$ is OH, $R_4$ is not methyl,
ii) when $R_2$ is OH, $R_4$, $R_6$ and $R_5$ are not at the same time hydrogen,
iii) when $R_2$ together with $R_1$ is an oxo group, $R_4$, $R_6$ and $R_5$ are not at the same time hydrogen;

and pharmaceutically acceptable salts and solvates thereof.

A further embodiment of the invention provides compounds of formula (I) and pharmaceutically acceptable salts and solvates thereof

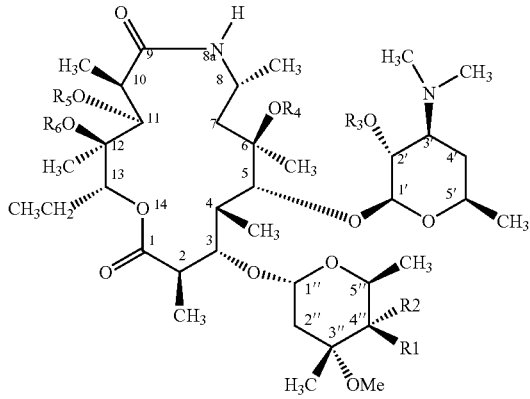

(I)

wherein $R_1$ is hydrogen or together with $R_2$ is oxo;

$R_2$ represents hydroxy, $OC(O)XR_7$, $OC(O)NHXR_7$ or $R_2$ together with $R_1$ is an oxo group;

$R_3$ is hydrogen or a hydroxyl protecting group;

$R_4$ is hydrogen or $XR_7$;

$R_5$ is hydrogen, $XR_7$, $C(O)XR_7$ or $C(O)NHXR_7$;

$R_6$ is hydrogen or $R_5$ and $R_6$ taken together with the intervening atoms form a cyclic carbonate having the following structure

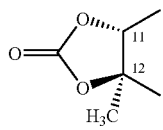

$R_7$ is selected from:
hydrogen,
optionally substituted phenyl,
optionally substituted 9 to 10 membered fused bicyclic carbocyclic ring,
optionally substituted 5 or 6 membered heterororaryl in which the 5-membered heteroaryl contains 1 or 2 heteroatoms selected from oxygen, sulphur or nitrogen and the 6-membered heteroaryl group contains 1 or 2 nitrogen atoms,
5-6 membered heterocyclic, or $R_7$ represents optionally substituted fused bicyclic heteroaryl containing 9 or 10 ring members having at least one heteroatom selected from oxygen, sulphur and nitrogen;

X is selected from:
a bond, $C_{1-12}$ alkylene (optionally substituted by one or two groups selected from a $C_{1-4}$ alkoxy, a halogen, a hydroxy or by a $NR_8R_9$), $C_{2-12}$ alkenyl group optionally substituted by one or two groups selected from a $C_{1-4}$ alkoxy, halogen, hydroxy or $NR_8R_9$ group or X represents a group $(CH_2)pY(CH_2)q$ wherein Y is $C(O)$, O, $S(O)n$ or $NR_8$;

$R_8$ and $R_9$ independently represent hydrogen, $C_{1-4}$ alkyl optionally substituted by a group selected from:
phenyl,
5-membered heteroaryl containing 1 or 2 heteroatoms selected from oxygen, sulphur or nitrogen or
$R_8$ and $R_9$ independently represent a phenyl optionally substituted by one or two $C_{1-4}$ alkyl, or a nitrogen protecting group;

n is 0 or an integer from 1 to 2;

p is an integer from 1 to 12; q is 0 or an integer from 1 to 11 with the proviso that the sum of p and q is an integer from 1 to 12; provided that
i) when $R_2$ is OH, $R_4$ is not methyl,
ii) when $R_2$ is OH, $R_4$, $R_6$ and $R_5$ are not at the same time hydrogen,
iii) when $R_2$ together with $R_1$ is an oxo group, $R_4$, $R_6$ and $R_5$ are not at the same time hydrogen;

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, fumarates and maleates.

The solvates may, for example, be hydrates.

References hereinafter to a compound according to the invention include both compounds of formula (I) and their pharmaceutically acceptable acid addition salts together with pharmaceutically acceptable solvates.

The compound of formula (I) and salts thereof may form solvates (e.g. hydrates) and the invention includes all such solvates.

In the general formula (I) as drawn the solid wedge shaped bond indicates that the bond is above the plane of the paper. The broken bond indicates that the bond is below the plane of the paper.

Compounds wherein $R_3$ represents a hydroxyl protecting group are in general intermediate for the preparation of other compounds of formula (I).

The term $C_{1-4}$ alkyl as used herein as a group or a part of the group refers to a straight or branched alkyl group containing from 1 to 4 carbon atoms; examples of such groups include methyl, ethyl, propyl, isopropyl, n-butyl, isobutyl, tert-butyl, 1-methyl ethyl or 2-methyl propyl.

The term $C_{1-6}$ alkylene is meant to include, but is not limited to, $C_{1-4}$ alkylene and the higher homologues thereof having 5 or 6 carbon atoms such as for example pentylene, 2-methylbutylene, hexyl, 2-methylpentylene, dimethylpropylene.

The term $C_{1-12}$ alkylene is meant to include, but is not limited to, $C_{1-6}$ alkylene and the higher homologues thereof having from 7 to 12 carbon atoms, such as for example n-heptylene, n-octylene, n-nonylene, n-decylene, n-undecylene and n-docecylene.

The term $C_{2-12}$ alkenyl chain refers to a straight or branched alkenyl chain containing from 2 to 12 carbon atoms and at least one double bond; examples of such groups include 2-propenyl, 1-propenyl, isopropenyl, 2-butenyl, 2-pentenyl, 2-hexenyl and the like.

The term $C_{3-7}$ cycloalkyl group means a non-aromatic monocyclic hydrocarbon ring of 3 to 7 carbon atom such as, for example, cyclopropyl, cyclobutyl, cyclopentyl, cyclohexyl or cycloheptyl.

When the group $OR_3$ is a protected hydroxyl group this is conveniently an ether or acyloxy group. Examples of particularly suitable ether groups include those in which $R_3$ is a trialkylsilyl (i.e trimethylsilyl). When the group $OR_3$ represents an acyloxy group, then examples of suitable groups $R_3$ include alkanoyl (i.e acetyl or benzoyl).

When $R_7$ is a 5 or 6 membered heteroaryl group according to the invention this include furanyl, thiophenyl, imidazolyl, oxazolyl, thiazolyl, pyrazolyl, pyridyl, pyridinium, pyridazinyl or pyrimidinyl.

When $R_7$ is a 5-6 membered heterocyclic group which is either saturated or unsaturated this may be a 3,6-dihydro-2H-pyridin-1-yl, a piperidin-1-yl, morpholyn-4-yl or a pyrrolidin 1-yl group.

The term halogen refers to a fluorine, chlorine, bromine or iodine atom.

The term $C_{1-4}$ alkoxy group may be a straight chain or a branched chain alkoxy group, for example methoxy, ethoxy, propoxy, prop-2-oxy, butoxy, but-2-oxy or methylprop-2-oxy.

When $R_7$ is 9 to 10 membered fused bicyclic carbocyclic this refers to a 5,6/6,5 or 6/6 bicyclic carbocyclic ring system which may be saturated or unsaturated.

Examples of such groups include naphthyl, 1, 2, 3, 4 tetrahydronaphthyl, indenyl or indanyl.

When $R_7$ is 9 to 10 membered fused bicyclic heteroaryl this include quinolyl, isoquinolyl, 1, 2, 3, 4 tetrahydroisoquinolyl, benzofuranyl, benzimidazolyl, benzothienyl, benzoxazolyl, 1,3 benzodioxazolyl, indolyl, benzothiazolyl, furylpyridine, oxazolopyridyl, benzofurany or benzothiophenyl.

When $R_7$ is a substituted phenyl, a substituted 5 or 6 membered heteroaryl or a substituted phenoxy group this refers to a group which is substituted by 1 to 3 groups selected from:

halogen, $C_{1-4}$ alkyl, $C_{1-4}$ alkoxy, hydroxy, nitro, cyano, amino, $C_{1-4}$ alkylamino or $diC_{1-4}$ alkylamino group or by one or two $(CH_2)mR_{10}$ wherein m is zero or an integer from 1 to 4 and $R_{10}$ is a group selected from:

hydroxy, $C_{1-4}$alkoxy, $C_{1-14}$alkanoyl-amino, $NR_{8a}R_{9a}$ (wherein $R_{8a}$ and $R_{9a}$ independently represent hydrogen or $C_{1-4}$alkyl), phenyl, phenoxy, 5-membered heteroaryl contains 1 or 2 heteroatoms selected from oxygen, sulphur or nitrogen and 6-membered heteroaryl containing 1 or 2 nitrogen atoms.

When $R_7$ is a substituted 9 to 10 membered fused bicyclic carbocyclic ring or is a substituted 9 to 10 membered fused bicyclic this refers to a group, which is substituted by one to 2 group selected from alkyl, halogen, cyano, nitro, trifluoromethyl and $NR_8R_9$.

When $R_8$ and $R_9$ independently represent a nitrogen protecting group this is conveniently alkoxycarbonyl e.g. t-butylcarbonyl, arylsulphonyl e.g. phenylsulphonyl or 2-trimetylsilylethoxy methyl.

Preferred compounds of formula (I) are those wherein $R_3$ is hydrogen.

A further preferred class of compounds of formula (I) is that wherein the group $C(O)XR_7$ represents a $C(O)XaR_7$ or a $C(O)X_bR_{7a}$ group and the group $OC(O)XR_7$, represents $OC(O)XaR_7$ or $OC(O)X_bR_{7a}$, wherein Xa is a group selected from $C_{1-12}$ alkylene (substituted by one or two groups selected from $C_{1-4}$ alkoxy, halogen, hydroxy or by $NR_8R_9$), $C_{2-12}$ alkenyl (optionally substituted by one or two groups selected from a $C_{1-4}$ alkoxy, halogen, hydroxy or by a $NR_8R_9$ group) or Xa represents a group $(CH_2)pY(CH_2)q$ wherein Y is C(O), O, S(O)n or $NR_8$;

$X_b$ is a bond or a $C_{1-12}$ alkylene chain;

$R_{7a}$ is a group selected from:
substituted phenyl,
optionally substituted phenoxy,
$C_{3-7}$ cycloalkyl,
substituted 9 to 10 membered fused bicyclic carbocyclic ring,
optionally substituted 5 or 6 membered heteroroaryl in which the 5-membered heteroaryl contains 1 or 2 heteroatoms selected from oxygen, sulphur or nitrogen and the 6-membered heteroaryl group contains 1 or 2 nitrogen atoms, 5-6 membered heterocyclic,
or
$R_{7a}$ represents optionally substituted fused bicyclic heteroaryl containing 9 or 10 ring members having at least one heteroatom selected from oxygen, sulphur and nitrogen;

$R_7$, $R_8$ or $R_9$ have the meanings defined in compounds of formula (I).

When $R_5$ is $XR_7$, $C(O)NHXR_7$ or when $R_4$ is $XR_7$, X is preferably $C_{1-6}$ alkyl ene (optionally substituted by $NR_8R_9$) or $C_{3-6}$ alkenyl (optionally substituted by $NR_8R_9$) or the group $(CH_2)pY(CH_2)q$ wherein Y is, O or $NR_8$ and the sum of p and q is an integer form 2 to 6.

When $R_2$ is $OC(O)XR_7$ or $OC(O)NHXR_7$, X is preferably $C_{1-6}$ alkylene (optionally substituted by $NR_8R_9$) or $C_{3-6}$ alkenyl (optionally substituted by $NR_8R_9$) or the group $(CH_2)pY(CH_2)q$ wherein Y is, O or $NR_8$ and the sum of p and q is an integer form 2 to 6.

When $R_5$ is $C(O)X_aR_7$, $C(O)X_bR_{7a}$ or when $R_2$ is $OC(O)X_aR_7$, $OC(O)X_bR_{7a}$ $X_a$ is preferably $C_{1-6}$ alkylene substituted by $NR_8R_9$, $C_{3-6}$ alkenyl (optionally substituted by $NR_8R_9$) or the group $(CH_2)pY(CH_2)q$ wherein Y is O or $NR_8$ the sum of p and q is an integer form 2 to 6; and $X_b$ is preferably $C_{1-6}$ alkylene.

When $R_5$ is $XR_7$, $C(O)XR_7$, $C(O)X_aR_7$, $C(O)NHXR_7$, when $R_4$ is $XR_7$ or when $R_2$ is $OC(O)XR_7$, $OC(O)X_aR_7$ or $OC(O)NHXR_7$, $R_7$ is preferably hydrogen, phenyl group (optionally substituted by one or two groups selected from halogen, nitro, trifluoromethoxy, cyano or 5 or 6 heteroaryl group), pyridyl, 3-quinolyl, 4-quinolyl, benzoxazolyl, 1,3 benzothiazolyl, 1,2,3,4-tetra hydroquinolyl, cyclopropyl, benzimidazolyl, isoquinolyl, naphthyl or furanyl.

When $R_5$ is $C(O)X_bR_{7a}$ or when $R_2$ is $OC(O)X_bR_{7a}$, $R_{7a}$ is a phenyl group (which is substituted by one or two groups selected from halogen, nitro, trifluoromethoxy, cyano or 5 or 6 heteroaryl group), pyridyl, 3-quinolyl, 4-quinolyl, benzoxazolyl, 1,3 benzothiazolyl, 1,2,3,4-tetra hydroquinolyl, cyclopropyl benzimidazolyl, isoquinolyl, naphthyl or furanyl.

A particular class of compound of formula (I) is that wherein $R_2$ is $OC(O)XR_7$ or $OC(O)NHXR_7$, X is $C_{1-6}$ alkylene (optionally substituted by $NR_8R_9$) or $C_{3-6}$ alkenyl (optionally substituted by $NR_8R_9$) or the group $(CH_2)pY(CH_2)q$ wherein Y is O or $NR_8$ and the sum of p and q is an integer form 2 to 6 and $R_7$ is hydrogen, phenyl group (optionally substituted by one or two groups selected from halogen, nitro, trifluoromethoxy, cyano or 5 or 6 heteroaryl group), pyridyl, 3-quinolyl, 4-quinolyl, benzoxazolyl, 1,3 benzothiazolyl, 1,2,3,4-tetra hydroquinolyl, cyclopropyl, benzimidazolyl, isoquinolyl, naphthyl or furanyl. Within this class the compounds, in which $R_2$ is $OC(O)X_aR_7$, $OC(O)X_bR_{7a}$, wherein $X_a$ is $C_{1-6}$ alkylene substituted by $NR_8R_9$, $C_{3-6}$ alkenyl (optionally substituted by $NR_8R_9$) or the group $(CH_2)pY(CH_2)q$ wherein Y is O or $NR_8$, and the sum of p and q is an integer form 2 to 6, $X_b$ is $C_{1-6}$ alkylene and $R_{7a}$ is phenyl (which is substituted by one or two groups selected from halogen, nitro, trifluoromethoxy, cyano or 5 or 6 heteroaryl group), pyridyl, 3-quinolyl, 4-quinolyl, benzoxazolyl, 1,3 benzothiazolyl, 1,2,3,4-tetra hydroquinolyl, cyclopropyl, benzimidazolyl, isoquinolyl, naphthyl or furanyl, are particularly preferred A preferred class of compounds of formula (I) is that wherein $R_5$ is hydrogen or in which $R_5$ and $R_6$ taken together with the intervening atoms forms a cyclic carbonate having the following structure.

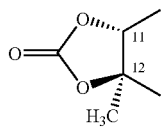

Within this class compounds in which $R_4$ is hydrogen, $C_{1-6}$ alkyl or $C_{3-6}$ alkenyl are particularly preferred.

An other preferred class of compounds of formula (I) is that wherein $R_4$ is hydrogen, $C_{1-6}$ alkyl or $C_{3-6}$ alkenyl.

A further particular class of compound of formula (I) is that wherein $R_5$ is C(O)X$R_7$, C(O)NHX$R_7$, $R_4$ is hydrogen or methyl, $R_2$ is OC(O)X$R_7$ or OC(O)NHX$R_7$, X is $C_{1-6}$ alkylene (optionally substituted by $NR_8R_9$) or $C_{3-6}$ alkenyl (optionally substituted by $NR_8R_9$) or the group $(CH_2)pY(CH_2)q$ wherein Y is O or $NR_8$ and the sum of p and q is an integer form 2 to 6, $R_7$ is hydrogen, phenyl group (optionally substituted by one or two groups selected from halogen, nitro, trifluoromethoxy, cyano or 5 or 6 heteroaryl group), pyridyl, 3-quinolyl, 4-quinolyl, benzoxazolyl, 1,3 benzothiazolyl, 1,2,3,4-tetra hydroquinolyl, cyclopropyl, benzimidazolyl, isoquinolyl, naphthyl or furanyl.

Within this class the compounds, in which $R_2$ is OC(O)$X_aR_7$, OC(O)$X_bR_{7a}$, $R_5$ is C(O)$X_aR_7$ or C(O)$X_bR_{7a}$, wherein $X_a$ is $C_{1-6}$ alkylene substituted by $NR_8R_9$, $C_{3-6}$ alkenyl (optionally substituted by $NR_8R_9$) or the group $(CH_2)pY(CH_2)q$ wherein Y is O or $NR_8$, p is 2 the sum of p and q is an integer form 2 to 6, $X_b$ is $C_{1-6}$ alkylene and $R_{7a}$ is a phenyl group (which is substituted by one or two groups selected from halogen, nitro, trifluoromethoxy, cyano or 5 or 6 heteroaryl group), pyridyl, 3-quinolyl, 4-quinolyl, benzoxazolyl, 1,3 benzothiazolyl, 1,2,3,4-tetra hydro-quinolyl, cyclopropyl, benzimidazolyl, isoquinolyl, naphthyl or furanyl, are particularly preferred.

A further particular class of compounds of formula (I) is that wherein $R_5$ is hydrogen, $R_5$ and $R_6$ taken together with the intervening atoms forms a cyclic carbonate, wherein $R_4$ is hydrogen, $C_{1-4}$ alkyl or $C_{3-6}$ alkenyl $R_2$ is OC(O)X$R_7$ or OC(O)NHX$R_7$, X is $C_{1-6}$ alkylene (optionally substituted by $NR_8R_9$) or $C_{3-6}$ alkenyl (optionally substituted by $NR_8R_9$) or the group $(CH_2)pY(CH_2)q$ wherein Y is O or $NR_8$ and the sum of p and q is an integer form 2 to 6, $R_7$ is hydrogen, phenyl group (optionally substituted by one or two groups selected from halogen, nitro, trifluoromethoxy, cyano or 5 or 6 heteroaryl group), pyridyl, 3-quinolyl, 4-quinolyl, benzoxazolyl, 1,3 benzothiazolyl, 1,2,3,4-tetra hydroquinolyl, cyclopropyl benzimidazolyl, isoquinolyl, naphthyl or furanyl.

Within this class the compounds, in which $R_2$ is OC(O)$X_aR_7$, OC(O)$X_bR_{7a}$, wherein $X_a$ is $C_{1-6}$ alkylene substituted by $NR_8R_9$, $C_{3-6}$ alkenyl (optionally substituted by $NR_8R_9$) or the group $(CH_2)pY(CH_2)q$ wherein Y is O or $NR_8$, p is 2, the sum of p and q is an integer form 2 to 6, $X_b$ is $C_{1-6}$ alkylene and $R_{7a}$ is phenyl (which is substituted by one or two groups selected from halogen, nitro, trifluoromethoxy, cyano or 5 or 6 heteroaryl group), pyridyl, 3-quinolyl, 4-quinolyl, benzoxazolyl, 1,3 benzothiazolyl, 1,2,3,4-tetra hydro-quinolyl, cyclopropyl, benzimidazolyl, isoquinolyl, naphthyl or furanyl, are particularly preferred Particular preferred compounds of the invention are:
4"-O-[3-(3-quinolyl)-2-ethenylcarbonyl]-6-O-methyl-8a-aza-8a-homoerythromycin A;
4"-O-(4-nitrophenylacetyl)-6-O-methyl-8a-aza-8a-homoerythromycin A;
4"-O-[3-(3-quinolyl)-2-ethenylcarbonyl]-8a-aza-8a-homoerythromycin A;
4"-O-[3-(1,2,3,4-tetrahydro-3-quinolyl)-ethyl-carbonyl]-6-O-methyl-8a-aza-8a-homo-erythromycin A;
4"-O-(4-(3-quinolyl)butanoyl)-6-O-methyl-8a-aza-8a-homoerythromycin A;
4"-O-(5-(3-quinolyl)-pentanoyl)-6-O-methyl-8a-aza-8a-homoerythromycin A;
4"-O-(5-(3-quinolyl)-4-pentenoyl)-6-O-methyl-8a-aza-8a-homoerythromycin A;
4"-O-[3-(3-quinolyl)-4-butenylcarbonyl]-8a-aza-8a-homoerythromycin A;
4"-O-(4-(3-quinolyl)-3-butenoyl)-6-O-methyl-8a-aza-8a-homoerythromycin A;
4"-O-(3-quinolyl)propenoyl-6-O-ethyl-8a-aza-8a-homoerythromycin A;
4"-O-(4-nitrophenyl)acetyl-6-O-ethyl-8a-aza-8a-homoerythromycin A;
4"-O-(p-Nitrophenylcarbamoyl)-6-O-methyl-8a-aza-8a-homoerythromycin A;

Compounds according to the invention also exhibit a broad spectrum of antibacterial activity against a wide range of clinical pathogenic microorganisms.

For example, using a standard microtiter broth serial dilution test, compounds of the invention have been found to exhibit useful levels of activity against a wide range of pathogenic microorganisms including *Staphylococcus aureus, Streptococcus pneumoniae, Moraxella catarrhalis, Streptococcus pyogenes, Haemophilus influenzae.*

Furthermore compounds of the invention are also active against intracellular pathogens such as *Chlamydia pneumonia, Clamydia* spp, *Legionella pneumophila, Mycoplasma pneumonia*, species.

The compounds of the invention may therefore be used for treating a variety of diseases caused by pathogenic bacteria in human beings and animals.

Thus, according to another aspect of the present invention, we provide a compound of formula (I) or a physiologically acceptable salt thereof for use in the therapy.

According to a further aspect of the invention we provide the use of a compound of formula (I) or a physiologically acceptable salt thereof for the manufacture of a therapeutic agent for the treatment or prophylaxis of systemic or topical bacterial infections in a human or animal body.

According to a yet further aspect of the invention we provide a method of treatment of the human or non-human animal body to combat bacterial infections which method comprises administering to the body an effective amount of a compound of formula (I) or a physiologically acceptable salt thereof.

While it is possible that, for use in therapy, a compound of the invention may be administered as the raw chemical it is preferable to present the active ingredient as a pharmaceutical formulation.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genito-urinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, eg dichlorodifluoromethane, trichlorofluoromethane, dichlorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01-99% of the active material. For topical administration, for example, the composition will generally contain from 0.01-10%, more preferably 0.01-1% of the active material.

For systemic administration the daily dose as employed for adult human treatment it will range from 2-100 mg/kg body weight, preferably 5-60 mg/kg body weight, which may be administered in 1 to 4 daily doses, for example, depending on the route of administration and the condition of the patient. When the composition comprises dosage units, each unit will preferably contain 200 mg to 1 g of active ingredient.

The duration of treatment will be dictated by the rate of response rather than by arbitrary numbers of days.

Compounds of general formula (I) and salts thereof may be prepared by general method outlined hereinafter. In the following description, the groups $R_1$, $R_2$, $R_3$, $R_4$, $R_5$, $R_6$, $R_7$, $R_8$, $R_9$, $R_{10}$, X, Y, n, m, p, and q have the meaning defined for the compounds of formula (I) unless otherwise stated.

Compounds of formula (I) wherein $R_2$ is a $OC(O)XR_7$ group may be prepared by reaction of compounds of formula (I) wherein $R_2$ is hydroxy

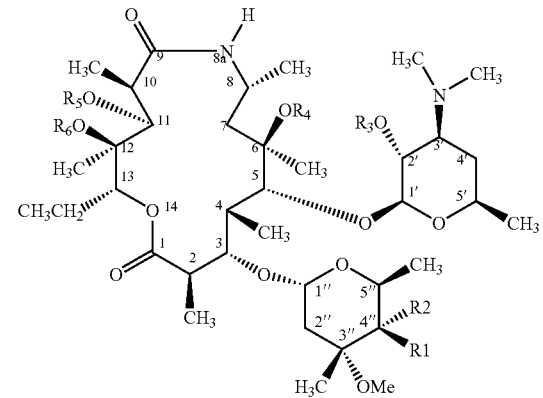

with a suitable activated derivative of the carboxylic acid (II), followed where necessary by subsequent removal of the hydroxyl protecting group $R_3$.

Suitable activated derivatives of the carboxyl group include the corresponding acyl halide, mixed anhydride or activated ester such as a thioester.

The reaction is preferably carried out in a suitable aprotic solvent such as a halohydrocarbon (e.g. dichloromethane) or N,N-dimethylformamide optionally in the presence of a tertiary base such as dimethylaminopyridine or triethylamine and at a temperature within the range of 0° to 120° C.

Compounds of formula (I) wherein $R_2$ is a $OC(O)NHXR_7$ group may be prepared by reaction of compounds of formula (I), wherein $R_2$ is hydroxy, with an isocyanate derivative (III) $R_7XNC(O)$ (III), followed where necessary by subsequent removal of the hydroxyl protecting group $R_3$.

The reaction with compound (III) is conveniently carried out in a solvent such as tetrahydrofuran, acetonitrile or halohydrocarbon (e.g dichloromethane).

Compounds of formula (I) wherein $R_2$ together with $R_1$ is an oxo group may be prepared by oxidation of the compound of formula (I), wherein $R_2$ is hydroxy, using a modified Moffat-Pfitzner procedure.

Suitable oxiding agent include N,N-dimethylaminopropyl-3-ethyl carbodiimide-dimethylsulfoxide. The reaction is suitably carried out in the presence of pyridiniumtrifluoro acetate in a chlorinated solvent such as methylene chloride at −10° C. to 25° C.

In a further embodiment, the oxidation may be carried out using Dess Martin periodinane reagent.

Alternatively compounds of formula (I) wherein $R_5$ and or $R_4$ is a $XR_7$ group may be prepared by reacting compounds of formula (I), in which $R_4$ represents hydrogen and $R_5$ represents a suitable hydroxyl protecting group, $XR_7$, $C(O)XR_7$ or $C(O)NHXR_7$ or in which $R_5$ is hydrogen and $R_4$ is a a suitable hydroxyl protecting group or a $XR_7$ group, $R_2$ is a protected hydroxy, $OC(O)XR_7$, $OC(O)NHXR_7$ or $R_2$ together with $R_1$ is a oxo group, with an alkylating compound of formula (IV) L-$XR_7$ (IV) in which L is a suitable leaving group such as a halogen (e.g chlorine, bromine or iodine) or a sulfonyl (e.g. tosyl, methansulfonyl), in the presence of a base, followed by removal of an hydroxyl protecting group.

The reaction with compound (IV) is preferably carried out in a solvent such as a halohydrocarbon (e.g. dichloromethane), an ether (e.g. tetrahydrofuran, dimethoxyethane), acetonitrile or ethyl acetate and the like.

Examples of the bases which may be used include potassium hydroxide, cesium hydroxide, tetraalkylammonium hydroxyde, sodium hydride, potassium hydride and the like.

In a further embodiment of the invention compounds of formula (1), wherein $R_5$ and or $R_4$ is a $XR_7$ group, may be prepared by chemical modification of initially prepared compounds of formula (I), wherein $XR_7$ is a 2-propenyl group (hereinafter referred to as 2-propenyl derivatives).

Examples of chemical modifications of 2-propenyl derivatives include, but are not limited to, catalytically reduction to give compounds of the invention wherein $XR_7$ is a propyl group, which can be then treated with osmium tetroxide to obtain compounds wherein $XR_7$ is 2,3 dihydroxylpropyl, which in turn may be further functionalized for example by esterification with an acylating agent such as an acyl chloride or acyl anhydride to give compounds of formula (I) wherein X is a 2-hydroxy propyloxy chain.

In a further embodiment, 2-propenyl derivatives may be converted to compounds of the invention wherein $XR_7$ is a 2-propenyl $R_7$ group, by reaction with a halide $R_7$ compound under Heck condition as described in Organic Reactions, 1982, 27, 345-390.

Alternatively, 2-propenyl derivatives may be oxidized for example with m-chloroperoxybenzoic acid in an aprotic solvent to give the corresponding epoxy methyl compounds which may be opened with nucleofilic compounds such as amines or N-containing heteroaryl compounds to give compound of formula (I) wherein $XR_7$ is a N-containing group.

In a further embodiment of the invention compounds of formula (I) wherein $R_2$ is a $OC(O)(CH_2)_2Y(CH_2)qR_7$ group in which Y is O or $NHR_8$ may be prepared by reaction of a compound of formula (I) wherein $R_2$ is $OC(O)$acriloyl with a compound of formula (V) $HY(CH_2)_qR_7$(V) wherein Y is O or $NHR_8$. The reaction is carried out in aprotic solvent such as acetonitrile.

In a further embodiment of the invention compounds of formula (I), wherein $R_5$ is a $C(O)NHXR_7$, may be prepared from compounds of formula (I), wherein $R_5$ and $R_6$ taken together with the intervening atoms form a cyclic carbonate (Ia), with amino derivatives of formula (VI) followed where necessary by subsequent removal of the hydroxyl protecting group $R_3$.

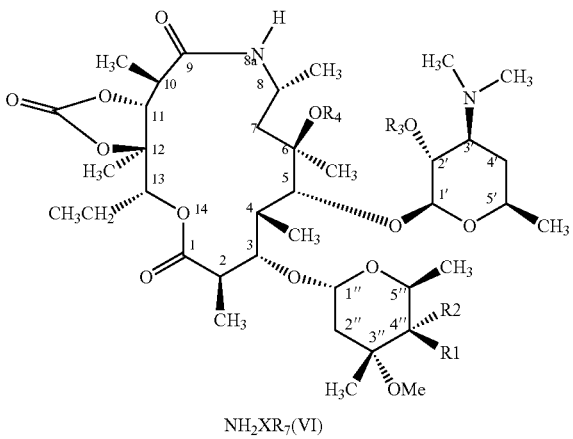

The reaction is preferably carried out in the presence of tertiary amine such as triethylamine, pyridine and in an aprotic solvent such as for example halohydrocarbon (e.g. dichloromethane), an ether (e.g. tetrahydrofuran, dimethoxyethane), acetonitrile or ethyl acetate and the like.

Alternatively, compound of formula (I) wherein $R_5$ is a $C(O)XR_7$ group may be obtained from compound of formula (I) in which $R_5$ is a hydrogen group by reaction with a suitable activated derivative of the carboxylic acid (II) using the reaction conditions above described, followed where necessary by subsequent removal of the hydroxyl protecting group $R_3$.

In a further process compounds of formula (Ia) wherein $R_5$ and $R_6$ taken together with the intervening atoms form a cyclic carbonate as above defined, may be prepared by reaction of compounds of formula (I) wherein $R_5$ is hydrogen group with ethylene carbonate or 1,1' carbonyldiimidazole in the presence of a base such as potassium or sodium carbonate, sodium hydroxy, or sodium hydride, followed by subsequent removal of the hydroxyl protecting group $R_3$. The reaction is conveniently carried out in a protic solvent such as tetrahydrofuran, acetonitrile or halohydrocarbon (e.g dichloromethane), ethyl acetate or N,N dimethylformamide.

Compounds of formula (I) wherein $R_5$ is a $XR_7$, a $C(O)XR_7$ or a $C(O)NHXR_7$ group and $R_2$ is hydroxy may be prepared by reaction of compound of formula (Ib), wherein $R_5$ is a hydrogen and $R_3$ and $R_{3a}$ are a hydroxyl protecting group as above defined

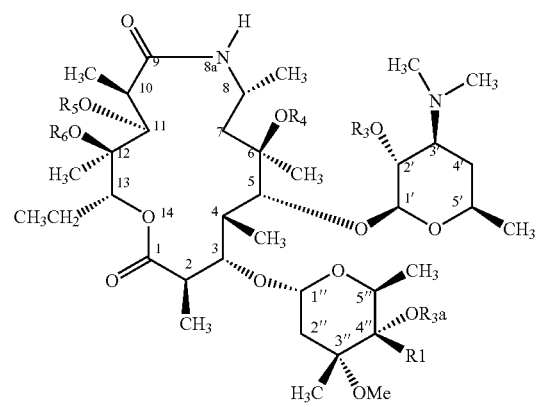

with an alkylating compound of formula (IV) L-$XR_7$ as above defined, an isocianate derivative $R_7$XNCO (III) or with a suitable activated derivative of the carboxylic acid HOC(O)XR$_7$ (II) respectively. The reaction conveniently takes place under the condition above described for preparing compounds of formula (I) wherein R$_5$ is a XR$_7$, a C(O)XR$_7$ or a C(O)NHXR$_7$ group.

Compounds of formula (I b), as defined above, may be obtained from compounds (I b), wherein R$_3$ and R$_{3a}$ are hydrogen, by reaction with a suitable hydroxy protecting reagent.

Suitable hydroxy protecting reagent are those described by T. W. Greene and P. G. M Wuts in Protective Groups in Organic Synthesis 2$^{nd}$ ed., John Wiley & Son, Inc 1991, which is incorporating by reference. Examples of suitable hydroxy protecting reagents include acetic anhydride, benzoic anhydride or a trialkylsilyl chloride in a protic solvent. Examples of aprotic solvent are dichloromethane, NN-dimethylformamide, dimethylsulfoxide, tetrahydrofuran and the like.

Compounds of formula (I), wherein R$_5$ and R$_3$ is hydrogen and R2 is hydroxy may be obtained by Beckmann rearrangement of erythromycin A oxime derivatives (VII) in which R$_{3b}$, R$_3$ and R$_{3a}$ is hydrogen.

(VII)

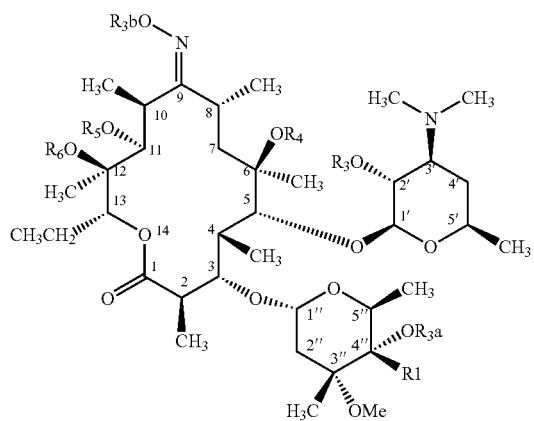

Example of suitable reagents catalyzing the rearrangement Beckmann include alkylsulphonyl halides such as methansulphonyl choloride or arylsulphonyl halides such as p-toluensulphonyl chloride, phenylsulphonyl chloride and the like. The reaction is carried out preferably in a solvent and in the presence of inorganic base (e.g. sodium hydrogencarbonate or potassiumcarbonate) or organic base such as pyridine. Suitable solvents include organic solvent such as an ether e.g. tetrahydrofuran, halohydrocarbon e.g. dichloromethane or acetonitrile or aqueous mixtures such as acetone-water or dioxan-water.

Oxime compounds (VII) may prepared by oximation of the oxo derivatives (VIII) wherein R$_3$ and R$_{3a}$ is hydrogen using analogous methods to those described in U.S. Pat. No. 6,110,965.

(VIII)

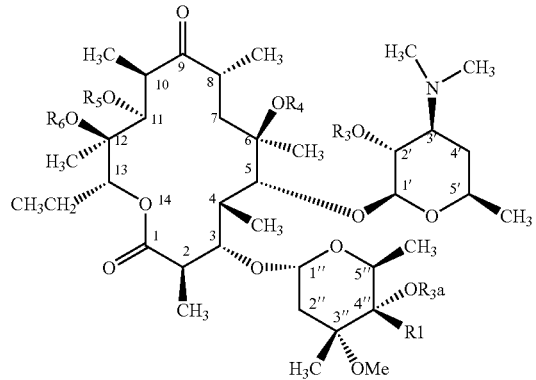

Compounds (VIII) in which R$_4$ is XR$_7$ may be prepared by alkylation of compounds of formula (VII) wherein R$_4$ is hydrogen, R$_{3b}$ is oxime protecting group and R$_3$ and R$_{3a}$ is a hydroxyl protecting group, with a compound of formula (IV) L-XR$_7$ (IV) in which L is a suitable leaving group using the procedures described above for obtaining compound of formula (I) wherein R$_5$ and or R$_4$ is XR$_7$ followed by subsequent removal of oxime protecting group. A suitable oxime protecting goup is R$_{3b}$ for example isopropylcyclohexyl.

Compounds of formula (II), (III), (IV) and (VIII) in which R$_4$ is hydrogen may be prepared by analogous methods to those used for known compounds.

Where it is desired to isolate a compound formula (I) as a salt thereof, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compound of formula (I) using conventional methods.

The hydroxyl and oxime protecting groups may be removed by well known standard procedures such as those described in T. W. Greene and P. G. M Wuts in Protective Groups in Organic Synthesis 2$^{nd}$ ed., John Wiley & Son, Inc. 1991. For example when R$_{3a}$ and R$_3$ are a trialkyllsilyl group, this may be removed by treatment with tetrabutylammonium fluoride and acetic acid or by reaction with fluoride ions source such as triethyl amine tris (hydrogen fluoride) or this process is conveniently carried out in a solvent such as tetrahydrofuran or acetonitrile. Similarly, when R$_{3a}$ and R$_3$ are alkanoyl (i.e acetyl or benzoyl) these may be removed by treatment with an alcohol (e.g methanol or ethanol).

The nitrogen protecting group may be removed by well known standard procedures such as those described in T. W. Greene and P. G. M Wuts in Protective Groups in Organic Synthesis 2$^{nd}$ ed., John Wiley & Son, Inc. 1991. Thus for example when R$_8$ and R$_9$ independently represent alkoxycarbonyl group may be removed by acid hydrolisis.

In order that the invention may be more fully understood the following examples are given by way of illustration only.

In the Preparations and Examples, unless otherwise stated:

Melting points (m.p.) were determined on a Büchi m.p. apparatus and are uncorrected. All temperatures refer to ° C.

Infrared spectra were measured in chloroform-d1 solutions on an FT-IR instrument.

Nuclear Magnetic Resonance spectra were recorded on Bruker Avance DRX 300 and DRX 500 as solutions in chloroform d-1, unless otherwise stated. Chemical shifts are reported in ppm. MS spectra Micromass were recorded on Platform LCZ.

Column chromatography was carried out over silica gel (Merck AG Darmstadt, Germany).

Solutions were dried over anhydrous sodium sulphate potassium carbonate. "Petrol" refers to petroleum ether, b.p. 40-60° C.

Methylene chloride was redistilled; tetrahydrofuran, ethyl acetate and DMF were dried over activated molecular sieves.

The following abbreviations are used in the text: PE=petroleum ether, EE=ethyl ether, EA=ethyl acetate, CH=cyclohexane, DCM=dichloromethane, MeCN=acetonitrile, THF=tetrahydrofurane, DMF=N,N-dimethyl formamide, MeOH=methyl alcohol, NMP=1-methyl-2-pyrrolidinone, TEA=triethylamine, DMAP=dimethylaminopyridine, EDC=1-ethyl-3-(3-Dimethylaminopropyl) carbodiimide.

Intermediate 1

6-O-allyl-2',4"-bis-O-trimethylsilylerythromycin A 9(Z)-[O-(1-isopropoxycyclohexyl)-oxime To a 0° C. solution of 2',4"-bis-O-trimethylsilylerythromycin A 9(Z)-[O-(1-isopropoxycyclohexyl)oxime] (2.5 g), in 40 ml of DMF freshly distilled allyl bromide (1.3 ml) was added. After approximately 5 minutes, potassium hydroxide (0.64 g) was added, portionwise, during about 20 minutes. After 2 hrs reaction was quenched with 20% solution of sodium hydroxide (40 ml), hexane (50 ml) was added and layers were separated. Water layer was extracted with hexane (2×40 ml). The combined organic extracts were washed with brine, dried over potassium carbonate, filtered and evaporated at reduced pressure, yielding the title compound (2.3 g)

TLC (Aceton/Hexan/TEA=1/5/0.001) Rf 0.49, MS (M+H) 1055

Intermediate 2

6-O-allyl-erythromycin A (E)(Z) 9-oxime (2a and 2b)

A mixture of intermediate 1 (2.3 g), MeOH (30 ml), water (60 ml) and acetic acid (pH 5) was stirred for 24 hrs at r.t. MeOH was evaporated at reduced pressure and residue extracted with methylene chloride (3×50 ml) at pH 9.8. The combined organic extracts were dried over potassium carbonate, filtered and evaporated at reduced pressure, yielding the title compound as a mixture of 9(Z)- and 9(E)-oximes. Such a mixture was purified by chromatography (ethylacetate-(n-hexane)-diethylamine 60:30:2) to obtain 9(E)-oxime (2a) (0.59 g)

Rf 0.647, ethylacetate-(n-hexane)-diethylamine 100:100:20, MS (M+H) 790.1, $^1$H NMR (500 MHz, CDCl$_3$) δ: 3.77 (H-8), 2.61 (H-10), 3.94 (6-O$\underline{CH_2}$), 5.92 (6-OCH$_2$$\underline{CH}$), 5.12 (6-O—CH$_2$CH=$\underline{CH_2}$), $^{13}$C NMR (75 MHz, CDCl3) δ: 25.3 (C-8), 32.9 (C-10), 79.2 (C-6), 65.7 (6-O$\underline{CH_2}$), 136.5 (6-OCH$_2$$\underline{CH}$), 115.5 (6-O—CH$_2$CH=$\underline{CH_2}$).

and 9(Z)-oxime (2b) (0.3 g)

Rf 0.571, ethylacetate-(n-hexane)-diethylamine 100:100:20, MS (M+H) 790.1, $^1$H NMR (500 MHz, CDCl$_3$) δ: 2.79 (H-8), 2.71 (H-10), 4.10 (6-O$\underline{CH_2}$), 5.91 (6-OCH$_2$$\underline{CH}$), 5.11 (6-O—CH$_2$CH=$\underline{CH_2}$), $^{13}$C NMR (75 MHz, CDCl3) δ: 38.6 (C-8), 34.2 (C-10), 79.3 (C-6), 65.1 (6-O$\underline{CH_2}$), 136.1 (6-OCH$_2$$\underline{CH}$), 116.0 (6-O—CH$_2$CH=$\underline{CH_2}$).

Intermediate 3

2'-O-acetyl-4"-O-trimetylsilyl-8a-aza-8a-homoerythromycin A 8a-aza-8a-homoerythromycin A (1.1 g, 0.0015 mol) was disolved in DCM (40 mL), than added acetic anhydride (1 eqv.) and left overnight at room temperature. Reaction mixture was washed with NaHCO3 aqueous solution (20 mL) and water (20 mL). After evaporation of the solvent to dryness 2'-O-acetyl-8a-aza-8a-homoerythromycin A was obtained (1.0 g) which was dissolved in CH$_2$Cl$_2$ (10 ml) and cooled to 0-5° C. Then pyridine (0.31 ml) and trimethylsilyl chloride (0.33 ml) were added and stirred for 2 hours at the same temperature. Upon the completion of the reaction, the reaction mixture was washed with NaH$_2$PO$_4$, water and brine, and reduced to dryness in vacuo affording 0.94 g of the title compound. Ms (ES) m/z: [MH]$^+$ 863

EXAMPLE 1

4"-O-(4-nitrophenylacetyl)-6-O-methyl-8a-aza-8a-homoerythromycin A

To a solution of 4-nitrophenylacetic acid (0.25 g) in DCM (3 ml) was added triethylamine (0.130 ml), and the resulting solution was cooled to 0° C. in an ice-water bath, under an argon atmosphere. To the cooled reaction solution pivaloyl chloride (0.115 ml) was added and the resulting mixture was stirred for 30 min. To the reaction mixture pyridine (0.3 ml) was added and then 2'-O-acetyl-6-O-methyl-8a-aza-8a-homoerythromycin A (0.25 g). The resulting mixture was stirred for 6 hrs, during which time the reaction mixture was allowed to warm to r.t. The reaction was quenched adding saturated sodium bicarbonate solution (20 ml), then DCM (20 ml) was added and aqueous layer was extracted with DCM (2×10 ml). The combined DCM extracts were washed with brine (20 ml) dried over potassium carbonate and concentrated in vacuo. The brown residue was purified via column chromatography EtOAc-hexane-Et2N=6:2:0.02, to obtain 290 mg of a brown foamy product which was dissolved in MeOH (15 ml) and stirred over night and then the solvent was concentrated in vacuo. The residue was purified by chromatography (MeOH-DCM-ammonia=5:90:0.5) to obtain the title compound (120 mg) as a brown-yellow solid.

Ms (ES) m/z: [MH]$^+$ 926.9

$^1$H NMR (500 MHz, CDCl$_3$) δ ppm 8.20 (H-Ph, 7.49 (H-Ph), 5.69 (8a-CONH), 5.07 (H-1"), 4.947 (H-13), 4.71 (H-4"), 4.55 (H-1'), 4.38 (H-5"), 4.17 (H-8), 3.99 (H-3), 3.83 (H—$\underline{CH_2}$Ph), 3.74 (H-5'), 3.73 (H—$\underline{CH_2}$Ph), 3.68 (H-5), 3.49 (H-11), 3.31 (H-3"-OMe), 3.28 (H-2'), 3.16 (H-OMe), 2.72 (H-3'), 2.70 (H-2), 2.48 (3'-NMe2), 2.39 (H-2"a), 2.29 (H-10), 1.93 (H-14a), 1.93 (H-4), 1.91 (H-4'a), 1.66 (H-7a), 1.63 (H-2"b), 1.54 (H-7b), 1.46 (H-14b), 1.36 (H-6Me), 1.31 (H-4'b), 1.24 (H-2Me), 1.20 (H-5'Me), 1.18 (H-10Me), (H-5"Me), 1.14 (H-8Me), 1.12 (H-3"Me), 1.06 (H-4Me), 1.04 (H-12Me), 0.90 (H-15).

$^{13}$C NMR (125 MHz, CDCl$_3$) δ ppm: 177.2, 174.4, 169.9, 147.3, 140.8, 130.3, 123.8, 102.3, 95.4, 80.3, 79.8, 78.8, 77.4, 77.2, 74.3, 73.0, 70.8, 70.4, 67.9, 65.5, 62.8, 51.8, 49.5, 45.4, 42.9, 42.4, 42.2, 41.0, 40.835.1, 23.8, 21.6, 21.6, 21.2, 17.9, 16.2, 15.0, 11.2, 9.7, 9.5

EXAMPLE 2

4"-O-[3-(3-quinolyl)-2-ethenylcarbonyl]-6-O-methyl-8a-aza-8a-homoerythromycin A

To a solution of 2'-O-acetyl-6-O-methyl-8a-aza-8a-homoerythromycin A (500 mg) in DMC (5 ml) and dry DMF (7.5 ml) 3-(3-quinolyl) acrylic acid (740 mg) was added and the resulting white suspension was cooled to 0° C. under an argon atmosphere. To the reaction mixture EDC hydrochloride (720 mg) was added in one portion, followed by addition of DMAP (75 mg). The reaction mixture was stirred for 2 days at r.t. The reaction was quenched adding saturated sodium bicarbonate (30 ml), then DMC (20 ml) was added and pH of resulting solution was adjusted to 9.5 with 2N NaOH. The aqueous layer was extracted with DMC (2×20 ml). The combined DMC extracts were washed with brine (20 ml), dried over potassium carbonate and concentrated in vacuo.

The brown residue was dissolved in MeOH (30 ml) and was stirred over night, and then the solvent was concentrated in vacuo. The residue was purified by chromatography (MeOH-EA=8:2) to obtain the title compound (420 mg) as a yellow solid.

Ms (ES) m/z: [MH]+ 945.1

$^1$H NMR (500 MHz, CDCl$_3$) δ ppm: 9.11(Q-2), 8.24 (Q-4), 8.12 (Q-8), 7.89 (Q-CH=CH), 7.87 (Q-5), 7.78 (Q-7), 7.61 (Q-6), 6.71 (Q-CH=CH), 5.69 (8a-CONH), 5.11 (H-1"), 4.97 (H-13), 4.85 (H-4"), 4.56 (H-1'), 4.47 (H-5"), 4.19 (H-8), 4.01 (H-3), 3.79 (H-5'), 3.71 (H-5), 3.52 (H-11), 3.37 (H-3"-OMe, 3.20 (H-2'), 3.18 (s, 6-OMe), 2.71 (H-2), 2.61 (H-3'), 2.45 (H-2"a), 2.35 (3'-NMe2), 2.27 (H-10), 1.93 (H-10), 1.93 (H-14a), 1.74 (H-4'a), 1.69 (H-7a), 1.69 (H-2"b), 1.59 (H-7b), 1.47 (H-14b), 1.38 (H-6Me), 1.29 (H-4'b), 1.24 (H-2Me), 1.23 (H-5'Me), 1.20 (H-5"Me), 1.19 (H-3"Me), 1.18 (H-10Me), 1.13 (H-12Me), 1.13 (H-8Me), 1.11 (H-4Me), 0.9 (H-15).

$^{13}$C NMR (125 MHz, CDCl$_3$) δ ppm: 177.1, 174.4, 166.2, 148.7, 148.6, 142.4, 136.1, 130.8, 129.5, 128.4, 127.7, 127.2(2C), 119.3, 102.7, 95.6, 80.3, 79.2, 78.8, 77.8, 77.2, 74.3, 73.1, 70.9, 70.4, 68.2, 65.5, 63.1, 51.8, 49.6, 45.6, 43.0, 42.4, 42.3, 41.0, 40.41, 39.4, 35.2, 29.4, 23.8, 21.7, 21.7, 21.5, 21.2, 17.9, 16.2, 15.1, 14.1, 11.2, 9.6, 9.5.

EXAMPLE 3

4"-O-[3-(4-quinolyl)-2-ethenylcarbonyl]-6-O-methyl-8a-aza-8a-homo-erythromycin A To a solution of 2'-O-acetyl--6-O-methyl-8a-aza-8a-homoerythromycin A (50 mg) in DCM (1 ml) and dry DMF (1 ml) 3-(4-quinolyl) acrylic acid (740 mg) was added and the resulting white suspension was cooled to 0° C., under an argon atmosphere. To the reaction mixture EDC hydrochloride (73 mg) was added in one portion, followed by addition of DMAP (10 mg). The reaction mixture was stirred for 2 days at r.t. The reaction was quenched adding saturated sodium bicarbonate (10 ml), then DCM (10 ml) was added and pH of resulting solution was adjusted to 9.5 with 2N NaOH. The aqueous layer was extracted with DCM (2×10 ml). The combined DCM extracts were washed with brine (20 ml), dried over potassium carbonate and concentrated in vacuo. The brown residue was dissolved in MeOH (15 ml) and stirred over night, and then the solvent was concentrated in vacuo. The residue was purified by chromatography MeOH—EtOAc=8:2) to obtain the title compound (30 mg) as a yellow solid.

Ms (ES) m/z: [MH]+ 944.7

$^1$H NMR (500 MHz, CDCl$_3$) δ ppm: 8.97 (Q-2), 8.50 (Q-CH=CH), 8.17 (Q-8), 8.16 (Q-7), 7.79 (Q-7), 7.65 (Q-6), 7.54 (Q-3), 6.67 (Q-CH=CH), 5.66 (8a-CONH), 5.12 (H-1"), 4.96 (H-13), 4.87 (H-4"), 4.55 (H-1'), 4.46 (H-5"), 4.17 (H-8), 4.02 (H-3), 3.78 (H-5'), 3.71 (H-5), 3.51 (H-11), 3.37 (H-3"-OMe), 3.23 (H-2'), 3.18 (6-OMe), 2.71 (H-2), 2.68 (H-3'), 2.46 (H-2"a), 2.37 (3'-NMe2), 2.27 (H-10), 1.93 (H-4), 1.93 (H-14a), 1.76 (H-4'a), 1.70 (H-2"b), 1.67 (H-7a), 1.56 (H-7b), 1.47 (H-14b), 1.37 (H-6Me), 1.29 (H-4'b), 1.23 (H-5'Me), 1.203 (H-2Me), 1.20 (H-3"Me), 1.20 (H-3"Me), 1.20 (H-2"Me), 1.19 (H-10Me), 1.13 (H-8Me), 1.13 (H-12Me), 1.10 (H-4Me), 0.9 (H-15).

$^{13}$C NMR-spektar (125 MHz, CDCl$_3$) δ ppm: 177.2, 174.4, 165.8, 150.2, 148.8, 140.6, 139.7, 130.4, 129.9, 127.5, 125.9, 123.7, 123.2, 118.1, 102.5, 95.5, 80.3, 79.5, 78.9, 77.6, 77.2, 74.3, 73.2, 70.9, 70.5, 68.1, 65.5, 63.1, 51.9, 49.6, 45.6, 43.0, 42.5, 42.2, 41.1, 40.4, 35.2, 29.7, 23.9, 21.7, 21.3, 18.0, 16.2, 15.1, 11.2, 9.7, 9.5.

EXAMPLE 4

4"-O-[3-(3-quinolyl)-2-ethenylcarbonyl]-8a-aza-8a-homoerythromycin A

To a solution of 2'-O-acetyl--8a-aza-8a-homoerythromycin A (500 mg) in DCM (5 ml) and dry DMF (7.5 ml) 3-(3-quinolyl)acrylic acid (740 mg) was added and the resulting white suspension was cooled to 0° C., under an argon atmosphere. To the reaction mixture EDC hydrochloride (720 mg) was added in one portion, followed by addition of DMAP (75 mg). The reaction mixture was stirred for 2 days at r.t. The reaction was quenched adding saturated sodium bicarbonate (30 ml), then DCM (20 ml) was added and pH of resulting solution was adjusted to 9.5 with 2N NaOH. The aqueous layer was extracted with DCM (2×20 ml). The combined DCM extracts were washed with brine (20 ml) dried over potassium carbonate and concentrated in vacuo. The brown residue was dissolved in MeOH (30 ml) and was stirred over night, and then the solvent was concentrated in vacuo. The residue was purified by chromatography (MeOH-EA=8:2) to give the title compound (250 mg) as a yellow solid.

Ms (ES) m/z: [MH]+ 930.6

$^1$H NMR (500 MHz, CDCl$_3$) δ ppm: 9.101 (Q-2), 8.25 (Q-4), 8.11 (Q-8), 7.90 (Q-5), 7.89 (Q-CH=CH), 7.78 (Q-7), 7.61 (Q-6), 6.68 (Q-CH=CH), 6.06 (8a-CONH), 5.18 (H-1"), 4.94 (H-13), 4.86 (H-4"), 4.61 (H-1'), 4.45 (H-5"), 4.38 (H-3), 4.20 (H-8), 3.87 (H-5'), 3.62 (H-5), 3.52 (H-11), 3.35 (H-3"-OMe), 3.24 (H-2'), 2.68 (H-3'), 2.66 (H-2), 2.65 (s, 6-OMe), 2.43 (H-2"a), 2.41 (3'-NMe2), 2.37 (H-10), 1.94 (H-4), 1.91 (H-14a), 1.83 (H-4'a), 1.69 (H-2"b), 1.60 (H-7a), 1.1.53 (H-7b), 1.44 (H-14b), 1.41 (H-6Me), 1.29 (H-4'b), 1.22-1.18 (8Me, 5'Me, 5"Me, 2Me, 3"Me and 10 Me), 1.11 (H-4Me), 1.10 (12Me), 0.91 (H-15).

$^{13}$C NMR (125 MHz, CDCl$_3$) δ ppm: 177.4, 176.2, 165.8, 148.3, 148.3, 142.4, 141.9, 135.7, 130.5, 129.0, 128.1, 127.2, 126.2(2C), 118.9, 102.0, 94.3, 82.4, 78.9, 76.9, 76.5, 74.4, 73.6, 72.9, 70.2, 69.6, 67.8, 65.4, 62.6, 49.2, 45.3, 42.7, 42.1, 41.3, 40.2, 40.0, 34.7, 28.9, 27.4, 23.0, 21.4, 21.4, 20.9, 17.5, 15.9, 14.39, 10.9, 9.2, 8.9.

EXAMPLE 5

4"-O-(3-pyridylacetyl)-6-O-methyl-8a-aza-8a-homoerythromycin A

To a solution of 2'-O-acetyl-6-O-methyl-8a-aza-8a-homoerythromycin A (1.0 g) in DCM (10 ml) at 0° C., 3-Pyridylacetate hydrochloride (3.723 mmol), 1-Ethyl-3-(3-dimethylaminopropyl)carbodiimide (3.723 mmol) and 4-(dimethylamino)pyridine (1.241 mmol) were added and reaction mixture was stirred at r.t. for 2 hrs. The reaction mixture was washed with water at pH=10 (3×10 ml). The organic layer was washed with brine (50 ml) and dried (Na2SO4). The solvent was then removed in vacuo to give crude 2'acetyl 2'-O-acetyl-3-O-decladinosyl-6-O-methyl-8a-aza-8a-homoerythromycin A which was dissolved in MeOH and stirred for 10 hrs. MeOH is then removed in vacuo and crude product is purified by chromatography using DCM: MeOH: ammonia=90:3:0.3 to give the title compound (85 mg) as a whitesolid.

MS (M+H) 883.9, $^1$H NMR (300 MHz, CDCl$_3$) δ: 8.51, 8.49, 7.65, 7.26 (Py), 5.85 (8a-CONH), 5.04 (H-1"), 4.92 (H-13), 4.67 (H-4"), 4.37 (H-5"), 4.49 (H-1'), 4.17 (H-8), 3.96 (H-3), 3.70 (H-5'), 3.65 (H-5), 3.62 (4"-C$\underline{H}_2$-Py), 3.49 (H-11), 3.27 (3"-OMe), 3.15 (H-2'), 3.13 (6-OMe), 2.66 (H-2), 2.52 (H-3'), 2.34 (H-2" a), 2.29 (3'-NMe2), 2.25 (H-10), 1.91 (H-4), 1.91 (H-14a), 1.68 (H-7a), 1.68 (H-4'a), 1.62 (H-2"b), 1.55 (H-7b), 1.47 (H-14b), 1.34 (6-Me), 1.31 (5"-Me), 1.18 (5'-Me), 1.18 (2-Me), 1.18 (H-4'b), 1.16 (10-Me), 1.14 (12-Me), 1.09 (8-Me), 1.06 (4-Me), 0.98 (3"-Me), 0.86 (15-Me).

$^{13}$C NMR (75 MHz, CDCl3) δ: 176.8, 174.0, 170.0, 148.5, 148.4, 136.3, 129.0, 123.4, 102.3, 95.0, 80.1, 79.7, 78.4, 77.2, 76.7, 73.8, 72.5, 70.4, 70.0, 67.8, 62.4, 65.1, 51.4, 49.1, 45.4, 42.6, 42.6, 41.8, 40.5, 40.0, 38.0, 34.7, 28.5, 23.4, 23.4, 21.3, 21.3, 21.2, 20.9, 15.8, 14.6, 10.8, 9.2, 9.0.

EXAMPLE 6

4"-O-(p-Nitrophenylcarbamoyl)-6-O-methyl-8a-aza-8a-homoerythromycin A

To the solution of 2'-O-acetyl-6-O-methyl-8a-aza-8a-homoerythromycin A (300 mg) in Toluene (5 ml) p-Nitrophenylisocyanate (2.235 mmol) was added at r.t. and reaction mixture was stirred at 50° C. for 120 hrs. The reaction mixture was filtered and the solvent removed in vacuo. Crude product was dissolved in MeOH and stirred for 10 hrs. MeOH is then removed in vacuo and crude product is purified by chromatography using DCM:MeOH:ammonia=90:3:0.3 to give the title compound (85 mg) as a white-yellow solid.

MS (M+H) 969.8, $^1$H NMR (300 MHz, CDCl$_3$) δ: 7.61, 8.20 (Ph), 6.12 (8a-CONH), 5.00 (H-1"), 4.99 (H-13), 4.84 (H-2'), 4.66 (H-4"), 4.38 (H-5"), 4.52 (H-1'), 4.17 (H-8), 4.05 (H-5'), 3.90 (H-3), 3.60 (H-5), 3.60 (H-3'), 3.50 (H-11), 3.37 (3"-OMe), 3.15 (6-OMe), 2.72 (H-2), 2.47 (H-2" a), 2.42 (3'-NMe2), 2.26 (H-10), 2.12 (2'-OC=O—C$\underline{H}_3$), 1.95 (H-4), 1.95 (H-14a), 1.88 (H-4'a), 1.71 (H-2"b), 1.68 (H-7a), 1.54 (H-7b), 1.44 (H-14b), 1.38 (H-4'b), 1.35 (6-Me), 1.28 (5"-Me), 1.23 (5'-Me), 1.23 (2-Me), 1.23 (3"-Me), 1.19 (10-Me), 1.14 (12-Me), 1.10 (8-Me), 0.98 (4-Me), 0.87 (15-Me).

$^{13}$C NMR (75 MHz, CDCl3) δ: 174.8, 174.6, 169.8, 152.3, 143.5, 142.8, 124.8, 117.5, 101.1, 96.4, 82.4, 79.9, 79.6, 79.0, 76.9, 73.6, 73.0, 70.7, 70.2, 67.8, 62.7, 62.6, 51.1, 49.2, 45.1, 41.8, 41.8, 41.4, 40.8, 40.2, 35.2, 31.3, 23.3, 22.4, 21.3, 20.1, 20.1, 20.1, 17.2, 15.8.14.9, 10.5, 9.3, 9.5.

EXAMPLE 7

4"-O-(3-Trifluoromethylphenylcarbamoyl)-6-O-methyl-8a-aza-8a-homoerythromycin A To a solution of 300 mg 2'-O-acetyl-6-O-methyl-8a-aza-8a-homoerythromycin A (0.373 mmol) in 5 ml toluene 3-Trifluormethylphenylisocyanate (2.235 mmol) was added at r.t. and the reaction mixture was stirred at 50° C. for 120 hrs. The reaction mixture was filtered and the solvent removed in vacuo. Crude product was dissolved in MeOH and stirred for 10 hrs. MeOH is then removed in vacuo and crude product is purified by chromatography using DCM:MeOH:ammonia=90:3:0.3 to give the title compound (221 mg) as a white-yellow solid.

MS (M+H) 994.1, $^1$H NMR (300 MHz, CDCl$_3$) δ: 7.78, 7.59, 7.42, 7.32 (Ph), 5.83 (8a-CONH), 5.07 (H-1"), 4.97 (H-13), 4.65 (H-4"), 4.38 (H-5"), 4.48 (H-1'), 4.16 (H-8), 3.99 (H-3), 3.98 (H-5'), 3.68 (H-5), 3.50 (H-11), 3.35 (3"-OMe), 3.25 (H-2'), 3.17 (6-OMe), 2.82 (H-3'), 2.71 (H-2), 2.47 (3'-NMe2), 2.43 (H-2" a), 2.28 (H-10), 1.93 (H-4), 1.91 (H-14a), 1.72 (H-7a), 1.68 (H-2"b), 1.57 (H-7b), 1.46 (H-14b), 1.38 (6-Me), 1.25 (H-4'b), 1.23 (5"-Me), 1.23 (5'-Me), 1.23 (2-Me), 1.21 (3"-Me), 1.19 (10-Me), 1.14 (12-Me), 1.13 (8-Me), 1.09 (4-Me), 0.88 (15-Me).

$^{13}$C NMR (75 MHz, CDCl3) δ: 176.6, 174.4, 153.0, 138.4, 131.1, 129.4, 121.5, 119.9, 115.2, 102.8, 95.7, 80.1, 78.3, 79.6, 78.8, 77.0, 74.1, 73.2, 70.7, 70.3, 68.2, 65.1, 62.9, 51.7, 49.5, 45.5, 42.7, 42.2, 41.8, 41.0, 40.2, 35.1, 29.7, 23.6, 21.6, 21.4, 21.2, 21.0, 17.7, 16.0, 15.2, 10.9, 9.5, 9.5.

EXAMPLE 8

4"-O-(Chloroacetyl)-6-O-methyl-8a-aza-8a-homoerythromycin A

To a solution of 2'-O-acetyl-6-O-methyl-8a-aza-8a-homoerythromycin A (210 mg) in DCM (3 ml) chloroacetic acid (123 mg) was added and the resulting solution was cooled to 0° C. under an argon atmosphere. To the reaction mixture EDCHCl (250 mg) in one portion, followed by addition of DMAP (10 mg). The reaction mixture was stirred for 1.5 h. The reaction was quenched via addition saturated sodium bicarbonate (20 ml), than to the reaction mixture was added DCM (20 ml). pH of resulting solution was adjusted to 9.5 with 2N NaOH. The layers were separated and aqueous layer was extracted with DCM (2×20 ml). The combined DCM extracts were washed with brine (20 ml), dried over K2CO3 and concentrated in vacuo.

The brown residue was dissolved in MeOH (20 ml) and was stirred over night. The solvent was concentrated in vacuo. The residue was purified via column chromatography MeOH-DCM-NH4OH=4:90:0.5) to give the title compound (150 mg) as a yellow solid.

Ms (ES) m/z: [MH]$^+$ 839.8

$^1$H NMR (500 MHz, CDCl$_3$) δ ppm: 5.65 (8a-CONH), 5.08 (H-1"), 4.93 (H-13), 4.73 (H-4"), 4.55 (H-1'), 4.37 (H-5"), 4.20 (H-8), ), 4.13 (AB, C$\underline{H}_2$Cl), 4.07 (AB, C$\underline{H}_2$Cl), 4.00 (H-3), 3.72 (H-5'), 3.67 (H-5), 3.47 (H-11), 3.32 (H-3"OMe), 3.32 (H-2'), 3.15 (6-OMe), 2.83 (H-3'), 2.69 (H-2), 2.54 (3'-NMe2), 2.40 (H-2"a), 2.30 (H-10), 2.0-1.85 (H-4'a, H-4 and H-14a), 1.64 (H-2"b), 1.63 (H-7a), 1.51 (H-7b), 1.46 (H-14b), 1.35 (H-6Me), 1.29-1.09 (H-4'b, H-2Me, H-5'Me, H-5"Me, H-3"Me, H-10Me, H-12Me, H-8Me), 1.04 (H-4Me), 0.89 (H-15).

$^{13}$C NMR (125 MHz, CDCl$_3$) δ ppm: 177.0, 173.9, 166.7, 101.7, 94.8, 80.4, 79.8, 78.4, 76.8, 76.7, 73.9, 72.6, 70.4, 70.0, 67.3, 65.2, 62.4, 51.5, 49.1, 45.1, 42.5, 42.1, 41.8, 40.6, 40.3, 40.1, 34.6, 30.1, 29.3, 23.5, 21.3, 21.1, 20.8, 20.5, 17.5, 15.8, 14.6, 10.8, 9.2, 9.1

EXAMPLE 9

4"-O-Acriloyl-6-O-methyl-8a-aza-8a-homoerythromycin A

To a solution of 2'-O-acetyl-6-O-methyl-8a-aza-8a-homoerythromycin A (1.80 g) in dry toluene (30 ml), under argon atmosphere, TEA (2.90 ml) was added in one portion. To the reaction mixture 3-chloropropionyl chloride (0.63 ml) was added during several minutes. The reaction mixture was stirred for 2 hrs. Two more equivalents of TEA and one equivalent of 3-chloropropionyl chloride were added to the reaction solution and stirred for additional 2 hrs. The reaction was quenched via addition saturated sodium bicarbonate (60 ml). The layers were separated and aqueous layer was extracted with toluene (3×30 ml). The combined toluene extracts were washed with brine (20 ml) dried over potassium carbonate and concentrated in vacuo. The crude product, from the above step was dissolved in MeOH (100 ml) and the solution was stirred at r.t. for 24 hrs. The reaction mixture was heated to reflux and stirred for 2 hrs. The solvent was evaporated and the crude product was purified via flash chromatography (MeOH-DCM-NH4OH=5:90:0.5) to give the title compound (1.54 g) as a white solid.

Ms (ES) m/z: [MH]$^+$ 817.5

$^1$H NMR (300 MHz, CDCl$_3$) δppm: 6.46 ( C$\underline{H}$2=CHC(O)O, 6.14 46 (CH2=C$\underline{H}$C(O)O, 5.90 ( C$\underline{H}$2=CHC(O), 5.62 (8a-CONH), 5.08 (H-1"), 4.94 (H-13), 4.76 (H-4"), 4.57 (H-1'), 4.37 (H-5"), 4.15 (H-8), 4.00 (H-3), 3.68 (H-5'), 3.68 (H-5).

$^{13}$C NMR (75 MHz, CDCl$_3$) δ ppm: 177.0, 173.9, 165.5, 131.4, 127.6, 101.8, 94.8, 79.6, 78.4, 78.3, 76.7, 76.6, 73.9, 72.6, 70.5, 70.0, 67.4, 65.1, 62.7, 51.5, 49.1, 45.1, 42.5, 42.0, 41.9, 40.6, 40.1, 34.8, 34.6, 29.6, 23.5, 21.3, 21.1, 20.7, 20.5, 17.6, 15.8, 14.6, 14.1, 10.8, 9.3, 9.1.

EXAMPLE 10

4"-O-N-(2-pyridylmethyl)carbamoyl-6-O-methyl-8a-aza-8a-homoerythromycin A 11,12-Carbonate (10a)

4",11-Bis[N-(2-pyridylmethyl)carbamoyl]-6-O-methyl-8a-aza-8a-homoerythromycin A (10b)

A solution of intermediate 5 (200 mg) in (2-aminomethyl) pyridine (1.0 ml). The resulting mixture was stirred at r.t. for 3 hrs. DCM (30 ml) and H2O (30 ml) were added. The layers were separated, and the DCM layer was washed with H2O (2×20 ml), brine (2×20 ml) dried over potassium carbonate and concentrated in vacuo.

To the residue MEOH (20 ml) was added and stirred over night. The solvent was evaporated, and the crude product was purified via flash chromatography MeOH-DCM-NH4OH=5-90-0.5 to obtain EXAMPLE 10a (70 mg)
Ms (ES) m/z: [MH]$^+$ 924.0 and EXAMPLE 10b Ms (ES) m/z: [MH]$^+$ 1032.3

EXAMPLE 11

4"-O-[3-(3-quinolyl)-2-ethenylcarbonyl]-6-O-methyl-8a-aza-8a-homoerythromycin A 11,12-Carbonate To a solution of 11,12-cyclic carbonate 2'-O-acetyl-6-O-methyl-8a-aza-8a-homoerythromycin A (950 mg) in DCM (10 ml) and dry DMF (13 ml) 3-(3-quinolyl) acrylic acid (1360 mg) was added and the resulting white suspension was cooled to 0° C. under an argon atmosphere. To the reaction mixture EDC hydrochloride (140 mg) was added in one portion, followed by addition of DMAP (75 mg). The reaction mixture was stirred for 2 days at r.t. The reaction was quenched adding saturated sodium bicarbonate (50 ml), then DCM (50 ml) was added and pH of resulting solution was adjusted to 9.5 with 2N NaOH. The aqueous layer was extracted with DCM (2×20 ml). The combined DCM extracts were washed with brine (20 ml), dried over potassium carbonate and concentrated in vacuo.

The brown residue was dissolved in MeOH (30 ml) and was stirred over night, and then the solvent was concentrated in vacuo. The residue was purified by chromatography using DCM:MeOH:NH$_4$OH=90:3:0.3 to give the title compound (850 mg) as a white-yellow solid.

MS (M+H) 970.9, $^1$H NMR (300 MHz, CDCl$_3$) δ: 9.11, 8.26, 8.12, 7.92, 7.78, 7.61 (QI), 7.89 (4"-OCOCHC$\underline{H}$-QI), 6.75 (4"-OCOC$\underline{H}$CH-QI), 5.04 (H-1"), 4.96 (H-13), 4.87 (H-4"), 4.59 (H-1'), 4.45 (H-11), 4.42 (H-5"), 4.02 (H-3), 4.07 (H-8), 3.67 (H-5'), 3.63 (H-5), 3.38 (3"-OMe), 3.18 (6-OMe), 2.76 (H-2), 2.46 (H-2"a), 2.39 (H-10), 2.39 (3'-NMe2), 1.92 (H-4), 1.87 (H-14a), 1.85 (H-4'a), 1.85 (H-7a), 1.71 (H-2"b), 1.60 (H-14b), 1.55 (H-7b), 1.45 (12-Me), 1.36 (H-4'b), 1.35 (6-Me), 1.30 (10-Me), 1.26 (2-Me), 1.22 (5"-Me), 1.21 (5'-Me), 1.15 (8-Me), 1.15 (3"-Me), 1.01 (4-Me), 0.92 (H-15).

$^{13}$C NMR (75 MHz, CDCl3) δ: 175.5, 169.9, 166.1, 148.7, 148.7, 148.5, 142.6, 135.9, 130.7, 128.3, 128.3, 127.5, 127.5, 126.9, 118.9, 101.0, 96.4, 85.3, 82.1, 80.9, 79.9, 78.7, 77.9, 75.9, 73.1, 68.0, 63.1, 50.9, 49.5, 45.5, 41.6, 41.8, 41.2, 40.5, 40.5, 35.3, 31.3, 22.8, 22.3, 21.5, 21.1, 17.6, 17.6, 15.1, 14.1, 11.8, 10.2, 9.9,

EXAMPLE 12

11-Morpholinylethylcarbamoyl-4"-O-[3-(3-quinolyl) 2-ethenylcarbonyl]-6-O-methyl-8a-aza-8a-homoerythromycin A To a solution of 11-morpholinyethyl carbamate 2'-O-acetyl-6-O-methyl-8a-aza-8a-homoerythromycin A (138 mg) in DCM (1 ml) and dry DMF (1 ml) 3-(3-quinolyl) acrylic acid (214 mg) was added and the resulting white suspension was cooled to 0° C. under an argon atmosphere. To the reaction mixture EDC hydrochloride (207 mg) was added in one portion, followed by addition of DMAP (27 mg). The reaction mixture was stirred for 5 days at r.t. The reaction was quenched adding saturated sodium bicarbonate (20 ml), then DCM (20 ml) was added and pH of resulting solution was adjusted to 9.5 with 2N NaOH. The aqueous layer was extracted with DCM (2×20 ml). The combined DCM extracts were washed with brine (20 ml), dried over potassium carbonate and concentrated in vacuo to give the 148 mg of 2'-O-Acetyl-derivative of the title compounds as a brown-yellow solid MS (M+H) 1142:3.

The product was dissolved in MeOH (30 ml) and stirred overnight, and then the solvent was concentrated in vacuo. The residue was purified by chromatography (MeOH-DCM-ammonia=5:90:0.5) to give the title compound (105 mg) as a white solid.

MS (M+H) 1100.3.

EXAMPLE 13

4"-Oxo-6-O-methyl-8a-aza-8a-homoerythromycin A

To a solution of 2'-O-Acetyl-6-O-methyl-8a-aza-8a-homoerythromycin A (1.17 g) was dissolved in DCM (13 ml), added pyridine (0.265 ml) and heated at reflux. Dess-Martin periodinane reagent (2.8 g) was added in two portions and reaction mixture stirred for 3 hrs. The reaction was washed with saturated Na$_2$S$_2$O$_3$, sodium bicarbonate and brine, dried over K$_2$CO$_3$, and the solvent was removed under reduced pressure. The crude material was left in MeOH overnight, after which time the solvent was removed. The crude product (1.10 g) was purified by chromatography eluting with DCM-MeOH-ammonia solution 25% (90:9: 0.5) to give f the title compound (197 mg).
MS (M+H)$^+$: 761

EXAMPLE 14

6-O-allyl-8a-aza-8a-homoerythromycin A

Intermediate 2b (0.3 g) was dissolved in acetone (10 ml) and the solution was cooled to 0-5° C. Subsequently, solutions of p-toluenesulfonylchloride (0.51 g) in acetone (10 ml) and sodium hydrogen carbonate (0.45 g) in water (10 ml) were dropwise added thereto within 1 hour under stirring. The reaction mixture was stirred at room temperature for 8 hours, acetone was evaporated at reduced pressure and to the aqueos solution methylenechloride (10 ml) was added, whereupon it was extracted at pH 9.8. The combined organic extracts were washed with brine, dried over potassium carbonate and evaporated at reduced pressure, yielding the title compound (0.23 g)

Rf 0.535, ethylacetate-(n-hexane)-diethylamine 100:100: 20, MS (M+H) 789.6, $^1$H NMR (500 MHz, CDCl$_3$) δ: 6.32 (8a-CONH), 6.06 (6-OCH$_2$C$\underline{H}$), 5.15 (6-O—CH$_2$CH=C$\underline{H_2}$a), 5.07 (6-O—CH$_2$CH=C$\underline{H_2}$b), 4.98 (H-13), 4.95 (H-1"), 4.21 (H-8), 4.10 (H-5"), 4.01 (6-OC$\underline{H_2}$), 4.01 (H-3), 4.48 (H-5), 4.48 (H-11), 3.31 (3"-OMe), 3.19 (H-2'), 3.03 (H-4"), 2.74 (H-2), 2.52 (H-3'), 2.39 (H-2" a), 2.34 (3'-NMe2), 2.00 (H-4), 1.95 (H-7a), 1.75 (H-14a), 1.64 (H-4'a), 1.54 (H-2"b), 1.48 (H-14b), 1.40 (6-Me), 1.30 (5"-Me), 1.26 (5'-Me), 1.25 (12-Me), 1.23 (2-Me), 1.18 (10-Me), 1.15 (8-Me), 1.13 (4-Me), 0.87 (15-Me).

$^{13}$C NMR (75 MHz, CDCl3) δ: 175.8 (C-1), 174.5 (C-9), 137.6 (6-OCH$_2$C$\underline{H}$), 115.7 (6-O—CH$_2$CH=C$\underline{H_2}$), 103.3 (C-1'), 95.6 (C-1"), 81.4 (C-5), 80.2 (C-6), 79.9 (C-3), 78.1 (C-4"), 77.2 (C-13), 74.2 (C-12), 72.9 (C-3"), 70.9 (C-11), 70.8 (C-2'), 69.0 (C-5'), 65.9 (6-OC$\underline{H_2}$), 65.7 (C-5"), 65.6 (C-3'), 49.4 (3"-OCH3), 45.6 (C-2), 42.8 (C-7), 42.2 (C-10), 41.6 (C-8), 41.5 (C-4), 40.4 (3'-NMe2), 35.4 (C-2"), 28.9 (C-4'), 29.4, 24.6, 23.5, 21.6, 21.5, 21.2, 18.1, 16.3, 10.9, 9.5 (10×Me).

EXAMPLE 15

6-O-(1-(3-quinolyl)propen-3-yl)]-8a-aza-8a-homoerythromycin A

To a solution of example 14 (0.2 g) in acetonitrile (10 ml) were added palladium acetate (0.017 g) and tri-(O-tolyl) phosphine (0.046 g). The mixture was degassed by bubbling N$_2$ through it for 30 minutes and then were added 3-bromoquinoline (0.102 ml;) and triethylamine (0.106 ml;). The reaction mixture was sealed in a tube under nitrogen, heated at 50° C. for 2 hrs and at 90° C. for 3 days. The solvent was removed and the crude product was purified by chromatography EA-(n-hexane)-diethylamine (60:30:2) to give the title compound (0.038 g).

Rf 0.26, ethyl acetate-(n-hexane)-diethylamine (100:100: 20)

MS (M+H)$^+$ 916.8

$^1$H NMR (CDCl$_3$) δ: 9.03, 8.18, 8.06, 7.84, 7.65, 7.52 (6-O—CH$_2$—CH=CH-Q), 6.68 (6-O—CH$_2$—C$\underline{H}$=CH-Q), 6.45 (8a-NH), 6.32 (6-O—CH$_2$—CH=C$\underline{H}$-Q), 3.97 (6-O—C$\underline{H_2}$—CH=CH-Q).

$^{13}$C NMR (CDCl$_3$) δ: 149.6, 147.5, 132.5, 129.8, 129.1, 129.0, 128.0, 126.7 (6-O—CH$_2$—CH=CH-Q), 128.4 (6-O—CH$_2$—C$\underline{H}$=CH-Q), 129.8 (6-O—CH$_2$—CH=C$\underline{H}$-Q), 79.6 (C-6), 64.2 (6-O—C$\underline{H_2}$—CH=CH-Q).

EXAMPLE 16

2'-O-Acetyl-4"-O-Imidazolylcarbonyl-6-O-methyl-8a-aza-8a-homoerythromycin A 11,12-Carbonate A solution of 2'-O-acetyl-6-O-methyl-8a-aza-8a-homoerythromycin A (300 mg) in dry DMF (3 ml) and dry THF (0.6 ml) was cooled to 0° C. under an argon atmosphere. To the reaction solution was added 1,1'-carbonydiimidazole (480 mg) in one portion, followed by portionwise addition of NaH, 60% oil suspension (71 mg). The resulting mixture was stirred, under an argon atmosphere at 0° C. for 1 h. and then quenched by water (30 ml) The solid was filtered and dried to give the title compound (304 mg) as a white solid.
Ms (ES) m/z: [MH]$^+$ 925.9

EXAMPLE 17

11-benzyl carbamoyl-4"-O-[3-[(3-quinolyl)-benzylamino]-1-propion-1-yl l]-6-O-methyl-8a-aza-8a-homoerythromycin A A solution of example 11 (250 mg) and benzyl amine (1 ml) was stirred at room temperature for 24 hrs. The reaction mixture was then taken up into (30-50 ml) DCM and washed with water at pH=7 (5×50 ml). The organic layer was washed with brine (50 ml) and dried (Na$_2$SO$_4$). The solvent was then removed in vacuo to give crude product which was then purified by chromatography using DCM:MeOH:NH$_4$OH=90:3:0.3 to give the title compounds (189 mg) as a white-yellow solid.

Using the same general method described above for obtaining compound 17 the following compounds have been prepared.

EXAMPLE 18

11-(4-phenylbutyl)carbamoyl-4"-O-[3-(3-quinolyl)-(4-phenylbutyl)-propion-1-yl]-6-O-methyl-8a-aza-8a-homoerythromycin A Example 11 (250 mg) was reacted with 1 ml of 4-phenylbutylamine to give title compound (98 mg).
MS (M+H) 1268.9

EXAMPLE 19

11-(2-pyridylmethyl)carbamoyl-4"-O-[3-(3-quinolyl)(2-pyridylmethyl)) propion-1-yl]]-6-O-methyl-8a-aza-8a-homoerythromycin A Example 11 (250 mg) was reacted with 1 ml of 2-(aminomethyl)pyridine to give the title compound (137 mg).
MS (M+H) 1187.2

EXAMPLE 20

11-(1-propen-3-yl)carbamoyl-6-O-methyl-8a-aza-8a-homoerythromycin A

A solution of 11,12-cyclocarbonate-6-O-methyl-8a-aza-8a-homoerythromycin A (150 mg) in allylamine (2 ml) was stirred at room temperature for 2 h. The reaction mixture was then taken up into (50 ml) CH$_2$Cl$_2$, and washed with water at pH=7 (5×50 ml). The organic layer was washed with brine (50 ml) and dried (Na$_2$SO$_4$). The solvent was then removed in vacuo to give crude product which was then purified by column chromatography using $CH_2Cl_2$:MeOH:$NH_4OH$=90:3:0.3 to give of the title compound (104 mg) as a white-yellow solid.

MS (M+H) 846.7, $^1$H NMR (300 MHz, $CDCl_3$) δ: 5.86 (CH2=C<u>H</u>—), 5.18 (C<u>H</u>2=CH—), 5.00 (H-1"), 4.97 (H-13), 4.44 (H-1'), 4.21 (H-11), 4.03 (H-5"), 4.27 (H-3), 4.20 (H-8), 3.84 (CH2=CH—C<u>H</u>2-), 3.81 (H-10), 3.75 (H-5), 3.50 (H-5'), 3.33 (3"-OMe), 3.19 (H-2'), 3.28 (6-OMe), 3.02 (H-4"), 2.75 (H-2), 2.53 (H-3'), 2.44 (H-2"a), 2.33 (3'-NMe2), 2.02 (H-4), 1.78 (H-14a), 1.70 (H-4'a), 1.55 (H-7b), 1.53 (H-14b), 1.52 (H-2"b), 1.37 (6-Me), 1.34 (8-Me), 1.29 (5"-Me), 1.28 (10-Me), 1.24 (12-Me), 1.24 (3"-Me), 1.23 (5'-Me), 1.21 (2-Me), 1.21 (H-4'b), 1.04 (4-Me), 0.87 (15-Me).

$^{13}$C NMR (75 MHz, CDCl3) δ: 175.4, 173.5, 171.0, 134.1, 115.6, 102.7, 96.5, 79.6, 78.6, 78.5, 77.7, 77.7, 77.6, 75.3, 72.4, 70.3, 68.6, 65.7, 65.2, 60.6, 50.5, 49.1, 45.7, 43.2, 42.8, 42.6, 41.4, 39.4, 34.7, 28.6, 22.4, 21.8, 21.1, 20.8, 20.8, 17.8, 16.5, 14.8, 13.8, 10.9, 10.8.

Using the same general method described above for obtaining compound 17 the following compounds have been prepared

EXAMPLE 21

11-Benzylcarbamoyl-6-O-methyl-8a-aza-8a-homo-erythromycin A 11,12-cyclocarbonate-6-O-methyl-8a-aza-8a-homoerythromycin A (80 mg) was reacted with 1 ml of Benzylamine to give the title compound (73 mg).

MS (M+H) 896.9

EXAMPLE 22

11-Isobutylcarbamoyl-6-O-methyl-8a-aza-8a-homo-erythromycin A 11,12-cyclocarbonate-6-O-methyl-8a-aza-8a-homoerythromycin A (80 mg) was reacted with 1 ml of Isobutylamine to give the title compound (69 mg).

MS (M+H) 862.9, $^1$H NMR (300 MHz, $CDCl_3$) δ: 5.03 (11-OCON<u>H</u>), 5.01 (H-1"), 4.84 (H-11), 4.75 (H-13), 4.44 (H-1'), 4.31 (H-3), 4.07 (H-5"), 3.84 (H-8), 3.81 (H-5), 3.50 (H-5'), 3.34 (3"-OMe), 3.30 (6-OMe), 3.18 (H-2'), 3.06 ((CH$_3$)$_2$CHC<u>H</u>$_{a2}$—), 3.02 (H-4"), 2.98 ((CH$_3$)$_2$CHC<u>H</u>$_{b2}$—), 2.74 (H-2), 2.74 (H-10), 2.51 (H-3'), 2.43 (H-2"a), 2.32 (3'-NMe2), 2.08 (H-4), 1.80 (H-14a), 1.79 ((CH$_3$)$_2$C<u>H</u>CH$_2$—), 1.72 (H-4'a), 1.70 (H-7a), 1.63 (H-7b), 1.56 (H-2"b), 1.52 (H-14b), 1.38 (6-Me), 1.29 (8-Me), 1.29 (5"-Me), 1.26 (H-4'b), 1.24 (2-Me), 1.24 (5'-Me), 1.23 (12-Me), 1.23 (3"-Me), 1.18 (10-Me), 1.18 (4-Me), 0.92 ((C<u>H</u>$_3$)$_2$CHCH$_2$—), 0.87 (H-15).

$^{13}$C NMR (75 MHz, CDCl3) δ: 176.1, 174.3, 156.2, 103.6, 97.3, 80.5, 79.3, 79.3, 78.5, 78.1, 77.5, 76.1, 73.2, 71.1, 69.5, 66.0, 65.9, 51.2, 49.9, 49.0, 46.6, 44.1, 43.7, 43.5, 42.3, 40.7, 35.6, 29.2, 23.2, 22.5, 22.0, 21.7, 21.5, 20.3, 18.6, 15.6, 14.5, 11.6

EXAMPLE 23

11-(2-Pyridylmethyl)carbamoyl-6-O-methyl-carbamoyl-8a-aza-8a-homoerythromycin A 11,12-cyclocarbonate-6-O-methyl-8a-aza-8a-homoerythromycin A (80 mg) was reacted with 1 ml of 2-(Aminomethyl)pyridine to give the title compound (21 mg).

MS (M+H) 897.9

EXAMPLE 24

11-(2-Morpholinoethyl)carbamoyl-6-O-methyl-8a-aza-8a-homoerythromycin A 11,12-cyclocarbonate-6-O-methyl-8a-aza-8a-homoerythromycin A (80 mg) was reacted with 1 ml of N-(2-aminoethyl)morpholine to give the title compound (61 mg).

MS (M+H) 920.1

EXAMPLE 25

4"-O-(4-(3-quinolyl)butanoyl)-6-O-methyl-8a-aza-8a-homoerythromycin A

To a solution of 2'Acetyl-6-O-methyl-8a-aza-8a-homoerythromycin A (100 mg) in CH2Cl2 (1 ml) and DMF (1 ml) was added 4-(3-quinolyl)butanoic acid (130 mg) and cooled to 0° C., under an argon atmosphere, via application an external ice-water bath. To the reaction solution was added EDC HCl (119 mg) in one portion followed by DMAP (15 mg). The resulting mixture was stirred for 24 h. The reaction was quenched adding saturated sodium bicarbonate (20 ml), then dichloromethane (20 ml) was added and pH of resulting solution was adjusted to 9.5 with 2N NaOH. The aqueous layer was extracted with dichloromethane (2×20 ml). The combined dichloromethane extracts were washed with brine (20 ml), dried over potassium carbonate and concentrated in vacuo. The brown residue was dissolved in methanol (50 ml) and stirred over night, and then the solvent was concentrated in vacuo. The residue was purified by chromatography (methanol-EtOAc=2:8) to obtain the title compound (28 mg) as a yellow solid.

Ms (ES) m/z: [MH]$^+$ 960

EXAMPLE 26

4"-O-{3-[(2-morpholinoethyl)amino]-3-(3-quinolyl)propanoyl}-8a-aza-8a-homoerythromycin A To a solution of example 4 (40 mg) in N-(2-ethylamino) morpholine (0.5 ml) which was stirred at room temperature for two days, CH2CL2 (30 ml) and H2O (30 ml) were added. The layers were separated, and the dichloromethane layer was washed with H2O (2×20 ml), brine (20 ml), dried over K2CO3 and concentrated in vacuo. The residue was purified by chromatography on silica gel by using MeOH—CH2Cl2-NH4OH=5-90-0.5 to obtain the title compound (18 mg) as a yellow solid. Ms (ES) m/z: [MH]$^+$ 1060.

EXAMPLE 27

4"-O-(3-quinolylcarbonyl)-6-O-methyl-8a-aza-8a-homoerythromycin A

To a solution of 2'Acethyl-6-O-methyl-8a-aza-8a-homoerythromycin A (90 mg) in CH2Cl2 (0.8 ml) and DMF (08 ml) was added 3-quinolinecarboxylic acid (95 mg, 0,55 mmol) and than was cooled to 0° C., under an argon atmosphere, via application an external ice-water bath. To the reaction solution was added EDC HCl (106 mg) in one portion followed by addition of DMAP (14 mgl). The resulting mixture was stirred for 24 h. The reaction was quenched adding saturated sodium bicarbonate (20 ml), then dichloromethane (20 ml) was added and pH of resulting solution was adjusted to 9.5 with 2N NaOH. The aqueous layer was extracted with dichloromethane (2×20 ml). The combined dichloromethane extracts were washed with brine (20 ml), dried over potassium carbonate and concentrated in vacuo. The brown residue was dissolved in methanol (50 ml) and stirred over night, and then the solvent was concentrated in vacuo. The residue was purified by silica gel by using MeOH—CH2Cl2-NH4OH=5-95-0.5 to obtain the title compound (88 mg) as a white powder.

Ms (ES) m/z: [MH]$^+$ 918

EXAMPLE 28

4"-O-(5-(4-pentenoyl)-6-O-methyl-8a-aza-8a-homoerythromycin A

To a solution of 4-pentenoic acid (0.90 ml) in $CH_2Cl_2$ (4 ml) was added Et3N (0.259 ml), and the resulting solution was cooled to 0° C. in an ice-water bath, under an argon atmosphere. Pivaloyl chloride (0.220 ml) was Then added and the resulting mixture was stirred for 30 min. pyridine (0.3 ml), 2'Acetyl-6-O-methyl-8a-aza-8a-homoerythromycin A (300 mg) and DMAP (13 mg) were added. The resulting mixture was stirred for 4 hr, during which time the reaction mixture was allowed to worm to ambient temperature. At that time TLC analysis (MeOH—CH2Cl2-NH4OH=9:90:0.5) of the reaction mixture revealed presence of the starting macrolide. Additional amount of the mixed anhydride of 4-pentenoic acid (0.63 ml) in $CH_2Cl_2$ (1 ml), Et3N (0.086 ml) and pivaloyl chloride (0.073 ml) was prepared and added to the reaction mixture at 0° C., and stirred for additional 4 h. The reaction was quenched addition saturated NaHCO3 (20 ml), then to the reaction mixture was added CH2Cl2 (30 ml), separated layers and aqueous layer was extracted with CH2Cl2 (2×10 ml). The combined CH2Cl2 extracts were washed with brine (20 ml) dried over K2CO3 and concentrated in vacuo. The white solid residue was dissolved in methanol (70 ml) and stirred over night, and then the solvent was concentrated in vacuo. The residue was purified by silica gel by using MeOH—CH2Cl2-NH4OH=5-95-0.5 to obtain the title compound (263 mg) as a white powder.

Ms (ES) m/z: [MH]$^+$ 845

EXAMPLE 29

4"-O-(5-(3-quinolyl)-4-pentenoyl)-6-O-methyl-8a-aza-8a-homoerythromycin A

A solution of 4"O-(3-pentenoyl)-6-O-methyl-8a-aza-8a-homoerythromycin A (200 mg, 0.24 mmol, in 3 ml of dry DMF was deoxygenated with argon for 30 minutes at room temperature. To the reaction solution 3-bromquinoline (0.096 ml, 0.71 mmol), triethylamine (0.164 ml, 1.20 mmol), Pd(OAc)$_2$ (11 mg, 0.05 mmol) and tri-o-tolyl-phosphine (30 mg, 0.10 mmol) were added. The mixture than was heated at 80° C. for 18 h. To the reaction mixture was added H2O (20 ml) and extracted with EtOAc (3×20 ml). The organic layer was extracted with brine (50 ml), dried over K2CO3 and concentrated in vacuo. The residue was purified via column chromatography on silica gel by using EtOAc:MeOH=7:3 to afford the title compound (60 mg), as a white solid.

Ms (ES) m/z: [MH]$^+$ 972

EXAMPLE 30

4"-O-(5-(3-quinolyl)-3-pentenoyl)-6-O-methyl-8a-aza-8a-homoerythromycin A

To a solution of 6-O-methyl-8a-aza-8a-homoerythromycin A (50 mg) in toluene (1.5 ml) and DMF (0.02 ml) was added 4-(3-quinolyl)$_3$-butenoic acid (42 mg) and than was cooled to 0° C., under an argon atmosphere, via application an external ice-water bath. To the reaction mixture was added DPTC (42 mg) in one portion followed by addition of DMAP (7 mgl). The resulting mixture was stirred for 24 h. The reaction was quenched via addition saturated NaHCO3 (20 ml), than to the reaction mixture was added CH2Cl2 (10 ml), separated layers and aqueous layer was extracted with CH2Cl2 (2×10 ml). The combined CH2Cl2 extracts were washed with brine (20 ml) dried over K2CO3 and concentrated in vacuo. The brown residue was dissolved in methanol (30 ml) and stirred over night, and then the solvent was concentrated in vacuo. The residue was purified by silica gel by using EtOAc:MeOH=7:3 to obtain the title compound (27 mg) as a white powder. MS (ES) m/z: [MH]$^+$ 972.

EXAMPLE 31

4"-O-(4-(3-quinolyl)-3-butenoyl)-6-O-methyl-8a-aza-8a-homoerythromycin A

To a solution of (3-quinoline)-3-butenoic acid (132 g) in $CH_2Cl_2$ (2 ml) and DMF (0.1 ml) was added Et3N (0.088 ml), and the resulting solution was cooled to 0° C. in an ice-water bath, under an argon atmosphere. Pivaloyl chloride (0.076 ml) was then added and the resulting mixture was stirred for 30 min. To the reaction mixture was added pyridine (0.3 ml) and then 6-O-methyl-8a-aza-8a-homoerythromycin A (70 mg) and then DMAP (10 mg). The resulting mixture was stirred for 24 hr, during which time the reaction mixture was allowed to worm to ambient temperature. The reaction was quenched via addition saturated NaHCO3 (20 ml), than to the reaction mixture was added CH2Cl2 (30 ml), separated layers and aqueous layer was extracted with CH2Cl2 (2×20 ml). The combined CH2Cl2 extracts were washed with brine (20 ml) dried over K2CO3 and concentrated in vacuo. The brown residue was dissolved in methanol (30 ml) and stirred over night, and then the solvent was concentrated in vacuo. The residue was purified by silica gel by using EtOAc:MeOH=7:3 to obtain the title compound (38 mg) as a white solid.

Ms (ES) m/z: [MH]$^+$ 958

EXAMPLE 32

4"-O-(5-(3-quinolyl)-pentanoyl)-6-O-methyl-8a-aza-8a-homoerythromycin A

To a solution of 5-(3-quinoline)-pentanoic acid (0.141 g) in $CH_2Cl_2$(2 ml) was added Et3N (0.088 ml), and the resulting solution was cooled to 0° C. in an ice-water bath, under an argon atmosphere. Pivaloyl chloride (0.076 ml) was then added and the resulting mixture was stirred for 30 min. To the reaction mixture was added pyridine (0.2 ml) and than 6-O-methyl-8a-aza-8a-homoerythromycin A (100 mg) and than DMAP (14 mg). The resulting mixture was stirred for 24 hr, during which time the reaction mixture was allowed to worm to ambient temperature. At that time TLC analysis (MeOH—CH2Cl2-NH4OH=9:90:0.5) of the reaction mixture revealed absence of the starting macrolide. The reaction was quenched via addition saturated NaHCO3 (20 ml), than to the reaction mixture was added CH2Cl2 (30 ml), separated layers and aqueous layer was extracted with CH2Cl2 (2×30 ml). The combined CH2Cl2 extracts were washed with brine (20 ml) dried over K2CO3 and concentrated in vacuo. The brown residue was dissolved in methanol (30 ml) and stirred over night, and then the solvent was concentrated in vacuo. The residue was purified on silica gel by using EtOAc:MeOH=7:3 to obtain the title compound (22 mg) as a white solid.

Ms (ES) m/z: [MH]$^+$ 974.

EXAMPLE 32 b

4"-O-(3-(2,3-dihydro-1,3-benzothiazol-2-yl)pro-panoyl)-6-O-methyl-8a-aza-8a-homoerythromycin A To a solution of 3-(2,3-dihydro-1,3-benzothiazol-2-yl) propanoic acid (30 mg,) in $CH_2Cl_2$ (1 ml) was added Et3N (0.023 ml), and the resulting solution was cooled to 0° C. in an ice-water bath, under an argon atmosphere. To the reaction solution was added pivaloyl chloride (0.02 ml, 016 mmol) and the resulting mixture was stirred for 30 min. To the reaction mixture was added pyridine (0.05 ml) and then 6-O-methyl-8a-aza-8a-homoerythromycin A (30 mg). The resulting mixture was stirred for 24 hr, during which time the reaction mixture was allowed to worm to ambient temperature. The reaction was quenched via addition saturated NaHCO3 (20 ml), than to the reaction mixture was added CH2Cl2 (20 ml), separated layers and aqueous layer was extracted with CH2Cl2 (2×10 ml). The combined CH2Cl2 extracts were washed with brine (20 ml) dried over K2CO3 and concentrated in vacuo. The brown residue was dissolved in methanol (30 ml) and stirred over night, and then the solvent was concentrated in vacuo. The residue was purified on silica gel by using EtOAc:MeOH=7:3 to obtain the title compound (4 mg) as a brown solid. Ms (ES) m/z: $[MH]^+$ 952.

EXAMPLE 33

4"-O-{3-[4-(3-quinolyl)butoxy]propanoyl}-6-O-methyl-8a-aza-8a-homoerythromycin A To a solution of 4"-O-propenoyl 6-O-methyl-8a-aza-8a-homoerythromycin A (100 mg) in CH3CN (2.0 ml) was added 4-(3-quinoliy)-1-butanol (70 mg) and DBU (0.1 ml). This mixture was heated at 80° C. for 24 h. At that time additional amount of DBU (0.1 ml) was added and stirred for additional 24 h. The solvent was evaporated and the residue purified on an SPE-column (2.0 SiO2, Step gradi~t SPE starting with EtOAc and going to 30% MEOH in EtOAc. By this system excess of quinolyne reagents was removed. The macrolide was purified on silica gel by using EtOAc:MeOH=7:3 to obtain the title compound (22 mg) as a white solid. Ms (ES) m/z: $[MH]^+$ 1002.

EXAMPLE 34

2'-O-Acetyl-4"-O-(1H-1-imidazolylcarbonyl)-6-O-methyl-8a-aza-8a-homoerythromycin A 11,12-Carbonate A solution of 2'-O-acetyl-6-O-methyl-8a-aza-8a-homoerythromycin A (300 mg) in dry DMF (3 ml) and dry THF (0.6 ml) was cooled to 0° C. in an ice-water bath, under an argon atmosphere. To the reaction solution was added 1,1'-carbonylimidazole (480 mg) in one portion, followed by portionwise addition of NaH, 60% oil suspension (71 mg). The resulting mixture was stirred, under an argon atmosphere at 0° C. for 1 h. At that time TLC analysis of the reaction mixture revealed complete conversion of the starting material to a new product. The reaction was quenched by the dropwise addition of cold water (30 ml) during which compound precipitate. The precipitated solid was filtered and dried to give the title compound (304 mg) as a white solid.

Ms (ES) m/z: $[MH]^+$ 925.9

EXAMPLE 35

4"-O—N-(2pyridylmethyl)carbamoyl-6-O-methyl-8a-aza-8a-homoerythromycin A 11,12-Carbonate

EXAMPLE 36

4",11-Bis(N-(2pyridylmethyl)carbamate)-6-O-methyl-8a-aza-8a-homoerythromycin A

A solution of 2'-O-acetyl-4"-O-Imidazolcarbonyl-6-O-methyl-8a-aza-8a-homoerythromycin A 11,12-Carbonate (200 mg) in (2-aminomethyl)pyridine (1.0 ml). The resulting mixture was stirred atmosphere at room temperature for 3 h. At that time TLC indicated complete conversion of the starting material to a new product(s) to the reaction mixture was added CH2CL2 (30 ml) and H2O (30 ml). The layers were separated, and the dichloromethane layer was washed with H2O (2×20 ml), brine (20 ml), brine (20 ml) dried over K2CO3 and concentrated in vacuo.

To the residue was added MEOH (20 ml) and stirred over night. The solvent was evaporated, and the crude product was purified via flash chromatography on silica gel by using MeOH—CH2Cl2-NH4OH=5-90-0.5. Work up of the first chromatography fraction afforded example 35 (70 mg).

Ms (ES) m/z: $[MH]^+$ 924.0

Continuing elution of the chromatography column afforded example 36 (30 mg).

Ms (ES) m/z: $[MH]^+$ 1032.3

EXAMPLE 37

4"-O-[3-(1,2,3,4-tetrahydro-3-quinolyl)-ethyl-carbonyl]-6-O-methyl-8a-aza-8a-homoerythromycin A

EXAMPLE 38

4"-O-[3-(3-quinolyl)-ethylcarbonyl]-6-O-methyl-8a-aza-8a-homoerythromycin A

To a solution of Example 2 in EtOH (8 ml) AcOH-AcONa buffer (pH 5) was added dropwise to a pH value of 6.5 value. Then, catalyst Pd/C 10% (0.025 g) was added and the mixture was stirred under hydrogen pressure of $1.4 \times 10^5$ Pa for 4 hrs. The catalyst was filtered off, and the filtrate evaporated under reduced pressure. To the obtained residue $H_2O$ (10 ml) and $CH_2Cl_2$ (5 ml) were added and extraction at pH 6 was done. The organic extract was dried and evaporated to give a mixture of the two title compounds (0.054 g).

Purification by column chromatography (silica; $CH_2Cl_2$—MeOH—$NH_4OH$ 90:9:0.5) afforded example 37 [Rf=0.81, MS (M+H) 950] and example 38 [Rf=069, MS (M+H) 946,], TLC: $CH_2Cl_2$—MeOH—$NH_4OH$ 90:9:1.5,

EXAMPLE 39

4"-O-(4-butenylcarbonyl)-8a-aza-8a-homoerythromycin A

To a solution of 4-pentenoic acid (2.5 ml) in (20 ml) was added $Et_3N$ (0.7 ml, 5 eqv) and resulting mixture was cooled to 0° C. under argon atmosphere. Pivaloyl chloride (0.6 ml) was added into the solution, stirred for further 30 min and then pyridine (0.8 ml) and DMP (0.08 g) were added to the reaction mixture. After that, 2'-O-acetyl-6-OH-8a-aza-8a-homoerythromycin A (0.5 g) was added dropwise within 30 min and then pyridine (10 ml). Water (30 ml) was added to the mixture and extracted at pH 4 and 9. The organic extract at pH 4 gave after evaporation of solvent an oily residue (2.84 g), which was dissolved in MeOH (110 ml), stirred for 30 hrs. Then, methanol was removed under reduced pressure, yielding oily residue (2.71 g). The crude product was purified by column chromatography ($CH_2Cl_2$—MeOH—$NH_4OH$=90:90:0.5) to give the title compound (0.125 g).
Ms (ES) m/z: [MH]+ 845

EXAMPLE 40

4"-O-[3-(3-quinolyl)-4-butenylcarbonyl)-8a-aza-8a-homoerythromycin A

Example 39 (0.125 g) was dissolved in DMF (1.5 ml), then palladium (II) acetate (2.4 mg) and tri-o-tolylphosphine (6.4 mg) was added and the mixture stirred under argon for 20 min. In the solution 3-bromoquinoline (0.022 ml) and TEA (0.029 ml) were added, and the reaction mixture was stirred at 80° C. for 38 hrs. Extraction with EtOAc and evaporation yielded crude product (0.156 g). which after purification by column chromatography with EtOAc-n-$C_6H_{12}$-DEA=100:100:20, afforded the title compound. MS (M+H) 958.

EXAMPLE 41

11-O-[3-(3-quinolyl)-2-propenyl]-8a-aza-8a-homo-erythromycin A.

Intermediate 3. (0.9 g) and cis-3-(3-quinolyl)propenyl t-butyl carbonate (0.630 g) were charged to a 50 ml rotary evaporator flask. Toluene (18 ml) was charged to dissolve the solids. The solvent was removed under vacuum, the residue dissolved again in toluene (18 ml) and solvent removed under vacuum. The residue was dissolved in toluene (25 ml) and approximately 7 ml of solvent was removed under vacuum. The residual solution was transferred to a three-neck round-bottom flask and deoxygenated with argon. $Pd_2(dba)_3$ (40 mg) and dppb (37 mg,) were charged into solution and heated at 80° C. for 1 hour. The solvent was removed on the rotary evaporator, the residue was dissolved in methanol in (200 mL) o, acifidied with formic acid to pH 5 and left overnight The mixture was evaporated to dryness and separated by column chromatography with $CHCl_3$—MeOH-conc. ammonia (6:1:0.1) to provide the title compound (0.35 g) MS (M+H) 917.

EXAMPLE 42

11-O-[3-(3-quinolyl)-2-propenyl]-4"-O-(4-nitrophenylacetyl)-8a-aza-8a-homoerythromycin A To a solution of 4-nitrophenylacetic acid (0.35 g) in CH2Cl2 (15 ml) was added Et3N (0.26 ml) and resulting mixture was cooled to 0° C. under argon atmosphere. Pivaloyl chloride (0.23 ml) was added to the solution, stirred for further 30 min and then pyridine (4.0 ml) was added to the reaction mixture. 2'-O-acetyl-11-O-[3-(3-quinolyl)-2-propenyl]-8a-aza-8a-homoerythromycin A prepared with acetic anhydride from Example 41 (0.35 g,) in DCM (5 ml) was added dropwise within 15 min. The reaction mixture was stirred for 20 hrs. under argon. Water (30 ml) was added to the mixture and extracted at pH 4 and 9. The organic extract at pH 4 gave after evaporation of solvent an oily residue. (0.97 g), which was dissolved in 100 mL of methanol 12 hours at room temperature. Evaporation of reaction mixture yielded slurry residue. Purification by column chromatography (CH2Cl2-MeOH—NH4OH=90:9:1.5) gave the title compound. (0.14 g) MS (M+H) 1080.

EXAMPLE 43

11-O-[3-(3-quinolyl)-2-propenyl]-4"-oxo-8a-aza-8a-homoerythromycin A

Example 41 was dissolved in MeOH, (20 ml) and 0.042 mL of aceticanhydride f the reaction mixture was stirred for 12 hr at room temperature then it was was dissolved in DCM (8 ml), then NaHCO3 (0.30 g) and pyridine (0.06 ml) were added. To the reaction mixture Dess-Martin periodinane reagent (0.840 g) was added portionwise during 5 hrs and the mixture stirred for 20 hrs. Extraction with DCM gave 11-O-[3-(3-quinolyl)-2-propenyl]-2'-acetyl-4"-oxo-8a-aza-8a-homoerythromycin A (0.25 g), which after deprotection in MeOH (50 mL) at rt overnight gave (0.220 g) of title compound. The crude product was purified by column chromatography (CH2Cl2-MeOH—NH4OH=90:9:1.5) to give the title compound. (0.075 g) MS (M+H) 915.

EXAMPLE 44

11-O-[3-(3-quinolyl)-2-propenyl]-4"-O-propenoyl-8a-aza-8a-homoerythromycin A

Example 41 was dissolved in MeOH (20 mL)-(0.042 mL of acetic anhydride in of, 12 hr at r.t.). then was treated with 3-chloropropionyl chloride (0.070 mL) in dry toluene (5 mL), TEA (0.26 mL) in one portion. The reaction mixture was stirred for 0.5 hrs. The reaction was quenched via addition 15 mL of saturated sodium bicarbonate. The layers were separated and aqueous layer was extracted with toluene (10 mL). The combined toluene extracts were washed with brine (20 mL), dried over potassium carbonate and concentrated in vacuo. The crude product, from the above step was deprotected by dissolving in MeOH (60 mL) and stirring at r.t. for 24 hrs. The solvent was evaporated to give the title compound (0.25 g). MS (M+H) 971.

EXAMPLE 44

6-O-ethyl-8a-aza-8a-homoerythromycin A 3.76 g of mixture of 6-O-ethylerythromycin 9(E)- and 9(Z)-oximes and 5.69 g of $NaHCO_3$ were suspended in 230 ml of mixture of acetone:water=1:1 and cooled down to 0° C. The solution of 6.46 g of p-toluenesulphonyl chloride in 55 ml of acetone was added dropwise in 30 minutes period and the suspension was stirred for 15 hours allowing to warm up to room temperature. Acetone was evaporated under reduced pressure, 100 ml of DCM and 100 ml of water were added, pH was set to 9.5 with 2M NaOH, organic layer was washed with brine, dried over $K_2CO_3$ and evaporated. The residue was purified on silicagel column in system EA:n-hexane:diethylamine=600:300:20 yielding the title compound (0.835 g).
MS (ES+) 777.5 [MH]+

EXAMPLE 45

2'-O-acetyl-6-O-ethyl-8a-aza-8a-homoerythromycin A example 44(735 mg) was dissloved in 20 ml of DCM at room temperature. $NaHCO_3$ (358 mg) and acetic anhydride (98.4 μl) were added and the suspension was stirred at room temperature for 20 hours. 20 ml of saturated solution of $NaHCO_3$ was added, water layer was washed with DCM (2×10 ml), organic layer was washed with 20 ml of brine, dried over K$_2$CO$_3$ and evaporated under reduced pressure yielding the title compound (661 mg).

MS (ES+) 819.7 [MH]$^+$

EXAMPLE 46

2'-O-acetyl-4"-O-(4-nitrophenyl)acetyl-6-O-ethyl-8a-aza-8a-homoerythromycin A (4-nitrophenyl)acetic acid (110 mg) and triethylamine (85.5 µL) were dissolved in 5 mL of DCM, cooled to 0° C. in N$_2$, pivaloyl chloride (75.2 µL) were added and the mixture was stirred for 30 minutes. After that pyridine (108 µL) were added followed by addition of example 45 (100 mg) in DCM (5 mL) and DMAP (15 mg). Reaction mixture was stirred for 20 hours at room temperature and additional amounts of 4-nitrophenyl acetic acid (110 mg), TEA (85.5 µL) and pivaloyl chloride (75.2 µL) were added. After 20 hours of stirring, reaction was quenched by addition of saturated NaHCO$_3$, water layer was washed with DCM, organic layer was washed with brine, dried over K$_2$CO$_3$ and evaporated yielding the title compound (128 mg).

MS (ES+) 982.6 [MH]$^+$

EXAMPLE 47

4"-O-(4-nitrophenyl)acetyl-6-O-ethyl-8a-aza-8a-homoerythromycin A

Example 46 (148 mg) was dissolved in MeOH (10.mL) and stirred for 2 days. The reaction mixture was after evaporation of solvent purified on silicagel column in system DCM:methanol:aq. amonia=90:9:0.5 yielding the title compound (55 mg). MS (ES+) 940.4 [MH]$^+$

EXAMPLE 48

2'-O-acetyl-4"-O-(3-quinolyl)propenoyl-6-O-ethyl-8a-aza-8a-homoerythromycin A

Example 45 (100 mg) and 3-(3-quinolyl)propenoyl acid (146 mg) were dissolved in 6 mL of mixture DCM:DMF=1:1 and cooled to 0° C. in N$_2$. After that 1-ethyl-3-(3-dimethylaminopropyl)carbodiimide (140.4 mg) and 15 mg of dimethylaminopyridine (15 mg) were added and the reaction mixture was stirred for 15 hours at room temperature. Additional 1-ethyl-3-(3-dimethylaminopropyl) carbodiimide (70 mg) was added and stirred for 4 hours. The reaction was quenched by addition of saturated NaHCO$_3$, organic layer was washed with brine and evaporated yielding the title compound (119 mg).

MS (ES+) 1000.6 [MH]$^+$

EXAMPLE 49

4"-O-(3-quinolyl)propenoyl-6-O-ethyl-8a-aza-8a-homoerythromycin A 119 mg of example 48 was dissolved in MeOH (5 mL) and stirred for 2 days. The reaction mixture was purified on silicagel column in system dichloromethane:methanol:aq. amonia=90:9:0.5 yielding the title compound (44 mg).

MS (ES+) 958.5 [MH]$^+$

EXAMPLE 50

6-O-allyl-8a-aza-8a-homoerythromycin A

Intermediate 2 (4.25 g) and NaHCO$_3$ (6.34 g) were suspended in 250 ml of mixture of acetone:water=1:1 and cooled down to 0° C. The solution of of p-toluenesulphonyl chloride (7.19 g) in 55 ml of acetone was added dropwise in 30 minutes period and the suspension was stirred for 15 hours allowing to warm up to room temperature. Acetone was evaporated under reduced pressure, 100 ml of DCM and 100 ml of water were added, pH was set to 9.5 with 2M NaOH, organic layer was washed with brine, dried over K$_2$CO$_3$ and evaporated. The residue was purified on silicagel column in system ethyl-acetate:n-hexane:diethylamine=600:300:20 yielding the title compound (2.36 g).

MS (ES+) 789.4 [MH]$^+$

EXAMPLE 51

6-O-propyl-8a-aza-8a-homoerythromycin A

Example 50 (2.3 g) was dissolved in MeOH (40 mL) at pH 5-5.5, 0.82 g of 10% Pd/C was added and the mixture was hydrogenated at 20 bar pressure for 20 hours. Methanol was evaporated, DCM (50 ml) and water (50 ml) were added, pH was set to 9.5 using 1M NaOH, water layer was washed with 10 ml of DCM, organic layer was washed with 50 ml of brine, dried over K$_2$CO$_3$ and evaporated under reduced pressure yielding the title compound (1.84 g).

MS (ES+) 792.0 [MH]$^+$

EXAMPLE 52

2'-O-acetyl-6-O-propyl-8a-aza-8a-homoerythromycin A

Example 51 (390 mg) was dissloved in 20 ml of dichloromethane at room temperature. NaHCO$_3$ and acetic anhydride were added and the suspension was stirred at room temperature for 20 hours. 20 ml of saturated solution of NaHCO$_3$ was added, water layer was washed with dichloromethane (2×10 ml), organic layer was washed with 20 ml of brine, dried over K$_2$CO$_3$ and evaporated under reduced pressure yielding the title compound (372 mg).

MS (ES+) 833.4 [MH]$^+$

EXAMPLE 53

2'-O-acetyl-4"-O-(p-nitrophenyl)acetyl-6-O-propyl-8a-aza-8a-homoerythromycin A (4-nitrophenyl)acetic acid (100 mg) and triethylamine (84 µL) were dissolved in 5 mL of dichloromethane, cooled to 0° C. in N$_2$, pivaloyl chloride (74 µL) were added and the mixture was stirred for 30 minutes. After that pyridine (106 µL) were added followed by addition of example 52 (100 mg) in dichloromethane (5 mL) and dimethyl aminopyridine (15 mg). Reaction mixture was stirred for 20 hours at room temperature and additional amounts of 4-nitrophenyl acetic acid (100 mg), TEA (84 µL) and pivaloyl chloride (74 µL) were added. After 20 hours of stirring, reaction was quenched by addition of saturated NaHCO$_3$, water layer was washed with dichloromethane, organic layer was washed with brine, dried over K$_2$CO$_3$ and evaporated yielding the title compound (118 mg).

MS (ES+) 996.6 [MH]$^+$

EXAMPLE 54

4"-O-(p-nitrophenyl)acetyl-6-O-propyl-8a-aza-8a-homoerythromycin A (PL 14977)

Example 53 (118 mg) was dissolved in MeOH ( . . . mL) and stirred for 2 days. The reaction mixture was purified on silicagel column in system dichloromethane:methanol:aq. amonia=90:9:0.5 yielding the title compound (41 mg). MS (ES+) 954.6 [MH]$^+$

EXAMPLE 55

2'-O-acetyl-4"-O-(3-quinolyl)acriloyl-6-O-propyl-8a-aza-8a-homoerythromycin A

Example 52 (96 mg) and 3-(3-quinolyl)acriloyl acid (137 mg) were dissolved in 6 mL of mixture dichloromethane: N,N,-dimethylformamide=1:1 and cooled to 0° C. in $N_2$. After that 1-ethyl-3-(3-dimethylaminopropyl) carbodiimide (133 mg) and 15 mg of dimethylaminopyridine (15 mg) were added and the reaction mixture was stirred for 15 hours at room temperature. Additional 1-ethyl-3-(3-dimethylaminopropyl) carbodiimide (66 mg) was added and stirred for 4 hours. The reaction was quenched by addition of saturated $NaHCO_3$, organic layer was washed with brine and evaporated yielding the title compound (102 mg).

MS (ES+) 1014.6 [MH]$^+$

EXAMPLE 56

4"-O-(3-quinolyl)acriloyl-6-O-propyl-8a-aza-8a-homoerythromycin A

Example 55 (102 mg) was dissolved in MeOH (10.mL) and stirred for 2 days. The reaction mixture was purified on silicagel column in system dichloromethane:methanol:aq. amonia=90:9:0.5 yielding the title compound (21 mg).

MS (ES+) 972.5 [MH]$^+$

EXAMPLE 57

4"-O-(3-Quinolyl)propenoyl-6-O-allyl-8a-aza-8a-homoerythromycin A (PL 830

To a solution of Example 14 (120 mg) in CH2Cl2 (10 ml), acetic anhydride (0.018 ml) and sodium hydrogencarbonate (64 mg) were added and then stirred for 3 hours at r.t. After reaction was completed $H_2O$ (10 ml) was added. The layers were separated, water layer extracted with CH2Cl2 (2×10 ml). Combined organic layers were washed with saturated aqueous solution of NaCl (3×10 ml), dried over Na2SO4, filtered and evaporated at reduced pressure yielding 2'-O-acetyl-6-O-allyl-8a-aza-8a-homoerythromycin (100 mg) which was dissolved in CH2Cl2 (1 ml) and DMF (1.3 ml). To this solution 3-(3-quinolyl)acrylic acid (120 mg) was added and then stirred at 0° C. After 30 minutes EDCxHCl (116 mg), DMAP (15 mg) weres added and the reaction mixture was stirred at r.t. to complete conversion (about 24 hours). After reaction was completed CH2Cl2 (10 ml), H2O (5 ml) whereupon it was extracted at pH 10. Layers were separated, water layer extracted with CH2Cl2 (2×10 ml). Combined organic layers were washed with saturated aqueous solution of NaCl (3×10 ml), dried over Na2SO4, filtered and evaporated at reduced pressure to obtain 2'-O-acetyl-4"-O-(3-quinolyl)acriloyl-6-O-propyl-8a-aza-8a-homoerythromycin (90 mg), this compound was stirred in MeOH (50 ml) at r.t. for 24 hours, MeOH was evaporated at reduced pressure. The residue was chromatographed on silica gel column using system CH2Cl2-MeOH—NH3=90:4:0.4., to obtain the title compound (24 mg).

Rf 0.312, ethylacetate-(n-hexane)-diethylamine 100:100:20, MS (M+H) 970.7

EXAMPLE 58

4"-O-(3-Quinolyl)propenoyl-6-O-(1-(3-quinolyl)propen-3-yl)]-8a-aza-8a-homoerythromycin A To a solution of example 15 (100 mg) in CH2Cl2(10 ml), acetic anhydride (0.013 ml) and sodium hydrogencarbonate (46 mg) were added and then stirred for 3 hours at r.t. After reaction was completed H2O (10 ml) was added. The layers were separated, water layer extracted with CH2Cl2 (2×10 ml). Combined organic layers were washed with saturated aqueous solution of NaCl (3×10 ml), dried over Na2SO4, filtered and evaporated at reduced pressure yielding 2'-O-acetyl-6-O-[3-(3-quinolyl)allyl]-8a-aza-8a-homoerythromycin A (80 mg) which was dissolved in CH2Cl2 (1 ml) and DMF (1.3 ml). To this solution 3-(0.3-quinolyl)acrylic acid (83 mg) was added and then stirred at 0° C. After 30 minutes EDCxHCl (80 mg), DMAP (10 mg) were added and the reaction mixture was stirred at r.t. to complete conversion (about 24 hours). After reaction was completed CH2Cl2 (10 ml), H2O (5 ml) where upon it was extracted at pH 10. Layers were separated, water layer extracted with CH2Cl2 (2×10 ml). Combined organic layers were washed with saturated aqueous solution of NaCl (3×10 ml), dried over Na2SO4, filtered and evaporated at reduced pressure to obtain an Obtained oily product (90 mg) was stirred in MeOH (50 ml) at r.t. for 24 hours to remove 2'-protection, MeOH was evaporated at reduced pressure. By chromatography on silica gel column using system CH2Cl2-MeOH—NH3=90:4:0.4 the title compound (18 mg) was obtained.

Rf 0.429, ethylacetate-(n-hexane)-diethylamine 100:100:20, MS (M+H) 1097.8

EXAMPLE 59

4"-O-(Propenoyl)-8a-aza-8a-homoerythromycin A

2'-OAc 6-OH-8a-aza-8a-homoerythromycin A (290 mg) was dissolved in 10 ml toluene and the solvent was evaporated. This was performed 2 times. After that the residue was again dissolved in 15 ml toluene and stirred under argon. To this solution was added 470 μl TEA and 101 μl 3 chloropropionyl-chloride (in three portions in a period of 10 minutes). After 15 h 235 μl TEA and 50 μl of 3 chloropropionylchloride were added. 3 h later 170 μl TEA and 25 μl of 3 chloro-propionylchloride were added. After that 30 ml of sat. $NaHCO_3$ was added. Extraction with 3×20 ml of toluene. Drying and evaporation of the solvent yielded 2'-OAc-4"O-(Propenoyl)-8a-aza-8a-homoerythromycin A (261 mg) which was dissolved in 30 ml of MeOH and stirred over night to yield after evaporation of the solvent the title compound (300 mg).

MS (ES+) 803.1

EXAMPLE 60

4"-O-{3-(N-methyl-N-(4-nitrophenyl)aminopropanoyl}-8a-aza-8a-homoerythromycin A

To a solution of Example 59 (5 mg) in acetonitrile 200 μl. 5 eq of N-methyl-N-(4-nitrophenyl)amine-hydrochloride were added followed by the addition of 10 μl of DIPEA. This mixture was heated at 70° C. for 12-48 hours and cooled to room temperature and the scavanger resin [30 mg] (isocyanate polymer bound) and $CH_2Cl_2$ (600 µl) were added. After 2 days the resin is filtered off, washed with methanol (300 µl), $CH_2Cl_2$ (300 µl) and again with methanol (300 µl). The solvent was evaporated giving the title compound (4.3 mg). MS (ES+) 983.4.

EXAMPLE 61

4"-O-{3-(N-methyl-N-[2-(2-pyridylethyl]aminopropanoyl}-8a-aza-8a-homoerythromycin A 3.5 mg; MS 939

EXAMPLE 62

4"-O-{3-(6,7-dimethoxy-1,2,3,4-tetrahydro-2-isoguinolyl)propanoyl}-8a-aza-8a-homoerythromycin A 4.2 mg; MS 996.

EXAMPLE 63

4"-O-{3-(1R,2S)-3-methoxy-1-phenylpropan-1-ol) aminopropanoyl}-8a-aza-8a-homoerythromycin A 3.0 mg; MS 984.

EXAMPLE 64

4-O-{3-(3,5-dimethoxybenzyl)aminopropanoyl}-8a-aza-8a-homoerythromycin A 2.9 mg; MS 970.

EXAMPLE 65

4"-O-{3-(N-ethyl-N-(4-pyridylmethyl)aminopropanoyl}-8a-aza-8a-homoerythromycin A 3.5 mg; MS 939.

EXAMPLE 66

4"-O-{3-[4-(trifluoromethoxy)phenyl]benzyl-aminopropanoyl}-8a-aza-8a-homoerythromycin A 3.1 mg; MS 994.

EXAMPLE 67

4"-O-{3-[3-(trifluoromethoxy)phenyl]benzyl-aminopropanoyl}-8a-aza-8a-homoerythromycin A 3.2 mg; MS 994.

EXAMPLE 68

4"-O-{3-[1-(4-methoxyphenyl)-1-ethanone]aminopropanoyl}-8a-aza-8a-homoerythromycin A 2.5 mg; MS 968.

EXAMPLE 69

4"-O-{3-(4-ethyl-2-methoxyphenol)aminopropanoyl}-8a-aza-8a-homoerythromycin A 2.4 mg; MS 970.

EXAMPLE 70

4"-O-{3-[(2S)-)-3-phenylpropan-1-ol)-2yl]aminopropanoyl}8a-aza-8a-homoerythromycin A 2.6 mg; MS 954.

EXAMPLE 71

4"-O-{3-(4-methoxybenzyl)aminopropanoyl}-8a-aza-8a-homoerythromycin A 3.1 mg; MS 940.

EXAMPLE 72

4"-O-{3-(3,4-dimethoxyphenethyl)-aminopropanoyl}-8a-aza-8a-homoerythromycin A 3.3 mg; MS 984.

EXAMPLE 73

4"-O-{3-4-pyridylethyl)aminopropanoyl}-8a-aza-8a-homoerythromycin A 3.9 mg; MS 911.

EXAMPLE 74

4"-O-{3-pyridylethyl-3-aminopropanoyl}-8a-aza-8a-homoerythromycin A 3.6 mg; MS 911.

EXAMPLE 75

4"-O-{3-(4-methoxyphenethyl)aminopropanoyl}-8a-aza-8a-homoerythromycin A 3.4 mg; MS 954.

EXAMPLE 76

4"-O-{3-(3,4-dimethoxybenzyl)aminopropanoyl}-8a-aza-8a-homoerythromycin A 3.4 mg; MS 970.

EXAMPLE 77

4"-O-{3-(4-nitrophenethyl)aminopropanoyl}-8a-aza-8a-homoerythromycin A 4.2 mg; MS 969.

EXAMPLE 78

4"-O-{3-(2,4-dimethoxybenzyl)aminopropanoyl}-8a-aza-8a-homoerythromycin A 3.8 mg; MS 970.

EXAMPLE 79

4"-O-{3-(2-methoxybenzyl)aminopropanoyl}-8a-aza-8a-homoerythromycin A 3.6 mg; MS 940.

EXAMPLE 80

4"-O-{3-(1,3-benzodioxazol-5-yl-methyl)aminopropanoyl}-8a-aza-8a-homoerythromycin A 2.9 mg; MS 954.

EXAMPLE 81

4"-O-{3-(3,4,5-trimethoxybenzyl)aminopropanoyl}-8a-aza-8a-homoerythromycin A (3.3 mg); MS 1000.

EXAMPLE 82

4"-O-{3-(2-ethoxybenzyl)minopropanoyl}-8a-aza-8a-homoerythromycin A 3.9 mg; MS 954.

EXAMPLE 83

4"-O-{3-(1S)-1-(4-methoxyphenyl)ethyl)aminopropanoyl}-8a-aza-8a-homoerythromycin A 3.6 mg; MS 954.

EXAMPLE 84

4"-O-{3-(1R)-1-(4-methoxyphenyl)ethylamine-2-aminopropanoyl}8a-aza-8a-homoerythromycin A 3.5 mg; MS 954.

EXAMPLE 85

4"-O-{3-(1S)-1-(4-nitrophenyl)ethyl)aminopropanoyl}-8a-aza-8a-homoerythromycin A 4.2 mg; MS 969.

EXAMPLE 86

4"-O-{3-(1R)-1-(4-nitrophenyl)ethyl)aminopropanoyl}-8a-aza-8a-homoerythromycin A 4.3 mg; MS 969.

EXAMPLE 87

4"-O-{3-(4-nitrobenzyl)aminopropanoyl}-8a-aza-8a-homoerythromycin A 4.5 mg; MS 955.

EXAMPLE 88

4"-O-{3-(N-methyl-N-(4-nitrophenyl)aminopropanoyl}-8a-aza-8a-homoerythromycin A 4.3 mg; MS 983.

EXAMPLE 89

4"-O-{3-(2-pyridylmethyl)aminopropanoyl}-8a-aza-8a-homoerythromycin A 4.2 mg; MS 911

EXAMPLE 90

4"-O-{3-(2-pyridyl)ethyl)aminopropanoyl}-8a-aza-8a-homoerythromycin A 4.1 mg; MS 925.

EXAMPLE 91

4"-O-{3-(tetrahydro-2-furanon-3-yl)aminopropanoyl}-8a-aza-8a-homoerythromycin A 2.2 mg; MS 905.

EXAMPLE 92

4"-O-{3-cyclopropyl-aminopropanoyl}-8a-aza-8a-homoerythromycin A 3.5 mg; MS 860.

EXAMPLE 93

4"-O-{3-[6-(-2,2-dimethyl-1,3-dioxepan-5-ol)-aminopropanoyl}-8a-aza-8a-homoerythromycin A 3.0 mg; MS 964.

EXAMPLE 94

4"-O-{(4-[4-(3-pyridyl)-1H-1-imidazoyl]butyl-(3-aminopropanoyl)}-8a-aza-8a-homoerythromycin A 3.5 mg; MS 1019.

EXAMPLE 95

4"-O-{3-(L-Phenylalaninyl)propanoyl}-8a-aza-8a-homoerythromycin A 3.8 mg; MS 968.

EXAMPLE 96

4"-{3-(L-Asparaginyl)propanoyl}-8a-aza-8a-homoerythromycin A 2.2 mg; MS 936.

The above examples (Examples 61 to 96) were obtained starting from Example 59 (5 mg) and and 5 equivalents of amine, following the same procedure described for Example 60.

The amount of reagents (i.e. amine compound) for Exs 61 to 96 are listed in Table 1.

TABLE 1

| Example no. | Amine | amine (mg) |
|---|---|---|
| EX 61 | (2-pyridyl)ethyl-N(H)-CH₃ | 4.2 |

TABLE 1-continued
| Example no. | Amine | amine (mg) |
|---|---|---|
| Ex 62 | 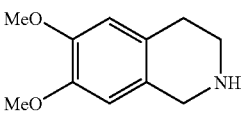 | 6.0 |
| Ex 63 | 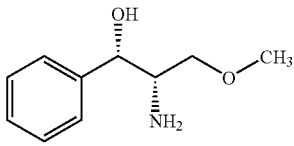 | 5.6 |
| Ex 64 | 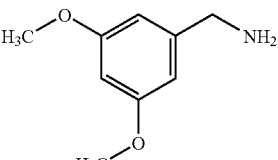 | 5.2 |
| Ex 65 | 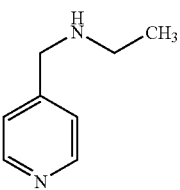 | 4.2 |
| Ex 66 | 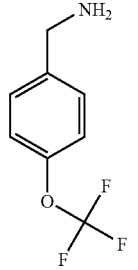 | 5.9 |
| Ex 67 | 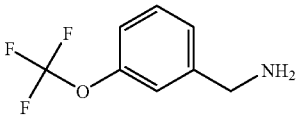 | 5.9 |
| Ex 68 | 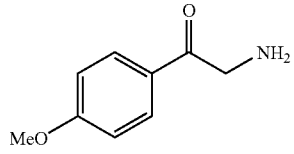 | 5.1 |
| Ex 69 | 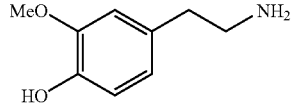 | 5.2 |
| Ex 70 | 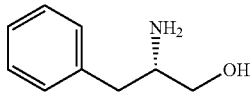 | 4.7 |
| Ex 71 | 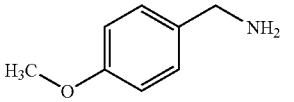 | 4.3 |
| Ex 72 | 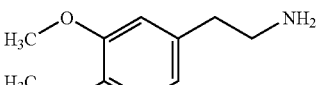 | 5.6 |
| Ex 73 | 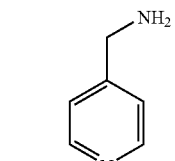 | 3.4 |
| Ex 74 | 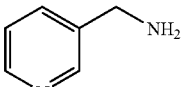 | 3.4 |
| Ex 75 | 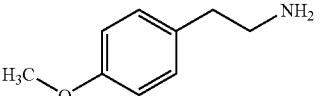 | 4.7 |
| Ex 76 | 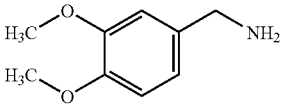 | 5.2 |
| Ex 77 | 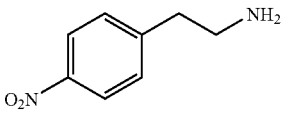 | 5.1 |
| Ex 78 | 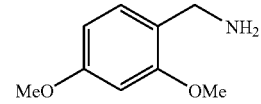 | 5.2 |
| Ex 79 | 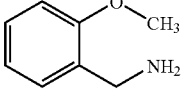 | 4.3 |
| Ex 80 | 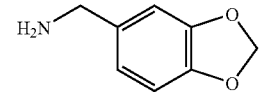 | 4.7 |
| Ex 81 | 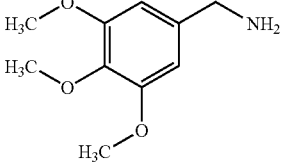 | 6.1 |

TABLE 1-continued

| Example no. | Amine | amine (mg) |
|---|---|---|
| Ex 82 | 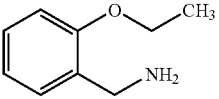 | 4.7 |
| Ex 83 | 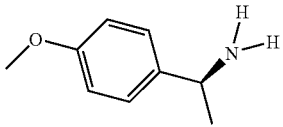 | 4.7 |
| Ex 84 | 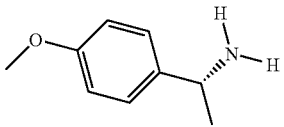 | 4.7 |
| Ex 85 | 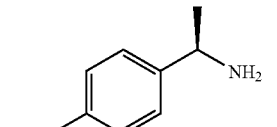 | 5.2 |
| Ex 86 | 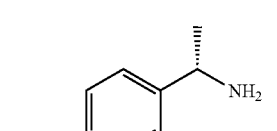 | 5.2 |
| Ex 87 | 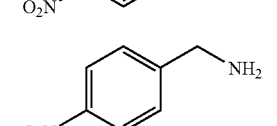 | 4.7 |
| Ex 88 | 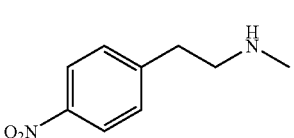 | 5.6 |
| Ex 89 | 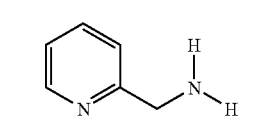 | 3.4 |
| Ex 90 | 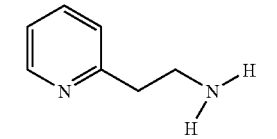 | 3.8 |
| Ex 91 | 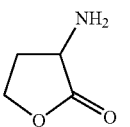 | 3.2 |
| Ex 92 | 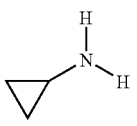 | 1.8 |
| Ex 93 | 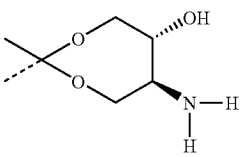 | 5.0 |
| Ex 94 | 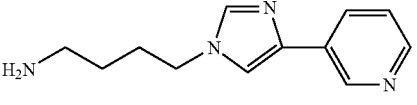 | 6.7 |
| Ex 95 | 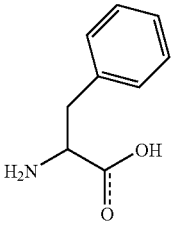 | 5.1 |
| Ex 96 | 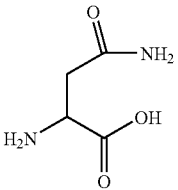 | 4.1 |

EXAMPLE 97

4″,11-O-(Dipropenoyl)-8a-aza-8a-homoerythromycin A

6-OH-8a-aza-8a-homoerythromycin A (2.0 g) was dissolved in 100 ml of $CH_2Cl_2$ at room temperature. To this solution 900 mg of $NaHCO_3$ and 280 µl of $Ac_2O$ were added. Stirring over night. To this mixture 100 ml of brine and 50 ml of water were added. The organic layer was separated, washed with 50 ml brine, dried and evaporated to yield 2′-OAc-4″,11-O-(Dipropenoyl) 8a-aza-8a-homoerythromycin A (2.1 g) 300 mg of this was dissolved in 10 ml toluene and the solvent was evaporated. This was performed 2 times. After that the residue was again dissolved in 15 ml toluene and stirred under argon. To this solution was added 470 µl TEA and 101 µl 3 chloropropionyl-chloride (in three portions in a period of 10 minutes). After 30 min 470 µl TEA and 101 µl 3 chloropropionyl-chloride (in three portions in a period of 10 minutes) were added. 3 h later 170 µl TEA and 25 µl of 3 chloro-propionylchloride were added. After that 30 ml of sat. $NaHCO_3$ was added. Extraction with 3×20 ml toluene. Drying and evaporation of the solvent yielded 301 mg of the product.

This residue was dissolved in 30 ml of MeOH and stirred over night to yield after evaporation of the solvent the title compound (280 mg).

MS (ES+) 803.1

EXAMPLE 98

4",11-O-Bis{3-(N-methyl-N-(4-nitrophenyl)amino-propanoyl}-8a-aza-8a-homoerythromycin A To a solution of example 97 (5 mg) in 200 μl of acetonitrile 10 eq of the amine N-methyl-N-(4-nitrophenyl)amine-hydrochloride were added, followed by the addition of 10 μl of DIPEA. This mixture was heated at 70° C. for 48 hours and cooled to room temperature and the scavanger resin [30 mg] (isocyanate polymer bound) and CH$_2$Cl$_2$ (600 μl) were added. After 2 days the resin is filtered off, washed with methanol (300 μl), CH$_2$Cl$_2$ (300 μl) and again with methanol (300 μl). The solvent was evaporated giving the title compound (4.2 mg).
MS (ES+) 1217.5

EXAMPLE 99

4",11-O-Bis{3-(N-methyl-N-[2-(2-pyridyl)ethyl]aminopropanoyl}-8a-aza-8a-homoerythromycin A 3.7 mg; MS 1129

EXAMPLE 100

4",11'-O-Bis{3-(6,7-dimethoxy-1,2,3,4-tetrahydroisoquinolin-2-yl)propanoyl}--8a-aza-8a-homoerythromycin A 4.0 mg; MS 1243

EXAMPLE 101

4",11-O-Bis{3-(1R,2S)-2-(2-amino-3-methoxy-1-phenylpropan-1-ol)propanoyl}--8a-aza-8a-homoerythromycin A 3.3 mg; MS 1219

EXAMPLE 102

4",11-O-Bis{3-(3,5-dimethoxybenzyl)aminopropanoyl}-8a-aza-8a-homoerythromycin A 3.2 mg; MS 1191

EXAMPLE 103

4",11-O-Bis{3-(N-ethyl-N-(4-pyridylmethyl)aminopropanoyl}-8a-aza-8a-homoerythromycin A 3.1 mg; MS 1129

EXAMPLE 104

4"11,-O-Bis{3-[4-(trifluoromethoxy)phenyl]benzylaminopropanoyl}-8a-aza-8a-homoerythromycin A 3.3 mg; MS 1239

EXAMPLE 105

4"11,-O-Bis{3-[3-(trifluoromethoxy)phenyl]benzylaminopropanoyl}-8a-aza-8a-homoerythromycin A 3.3 mg; MS 1239

EXAMPLE 106

4",11-O-Bis{3-[1-(4-methoxyphenyl)1-ethanone]aminopropanoyl}-8a-aza-8a-homoerythromycin A 2.2 mg; MS 1187

EXAMPLE 107

4",11-O-Bis{3-(4-ethyl)-2-methoxyphenol)aminopropanoyl}-8a-aza-8a-homoerythromycin A 2.9 mg; MS 1191

EXAMPLE 108

4",11-O-Bis{3-(2S)-3-phenylpropan-1-ol)aminopropanoyl}-8a-aza-8a-homoerythromycin A 3.1 mg; MS 1159

EXAMPLE 109

4",11-O-Bis{3-(4-methoxybenzyl-)minopropanoyl}-8a-aza-8a-homoerythromycin A 3.3 mg; MS 1131

EXAMPLE 110

4",11-O-Bis{3-(3,4-dimethoxyphenethyl)minopropanoyl}-8a-aza-8a-homoerythromycin A 3.5 mg; MS 1219

EXAMPLE 111

4",11-O-Bis{3-(4-pyridylethyl)aminopropanoyl}-8a-aza-8a-homoerythromycin A 3.1 mg; MS 1073

EXAMPLE 112

4",11-O-Bis{3-(3-pyridylethyl)minopropanoyl}-8a-aza-8a-homoerythromycin A 3.8 mg; MS 1073

EXAMPLE 113

4",11-O-Bis{3-(4-methoxyphenethyl)aminopropanoyl}-8a-aza-8a-homoerythromycin A 3.6 mg; MS 1159

EXAMPLE 114

4",11-O-Bis{3-(3,4-dimethoxybenzyl)aminopropanoyl}-8a-aza-8a-homoerythromycin A 3.5 mg; MS 1191

EXAMPLE 115

4",11'-O-Bis{3-(4-nitrophenethyl)aminopropanoyl}-8a-aza-8a-homoerythromycin A 4.1 mg; MS 1189

EXAMPLE 116

4",11'-O-Bis{3-(2,4-dimethoxybenzyl)aminopropanoyl}-8a-aza-8a-homoerythromycin A 3.6 mg; MS 1191

EXAMPLE 117

4",11-O-Bis{3-(2-methoxybenzyl)aminopropanoyl}-8a-aza-8a-homoerythromycin A 3.4 mg; MS 1131

EXAMPLE 118

4",11-O-Bis{3-(1,3-benzodioxazol-5-ylmethyl)aminopropanoyl}-8a-aza-8a-homoerythromycin A 2.6 mg; MS 1159

EXAMPLE 119

4",11-O-Bis{3-(3,4,5-trimethoxybenzyl)aminopropanoyl}-8a-aza-8a-homoerythromycin A 3.3 mg; MS 1251

EXAMPLE 120

4",11-O-Bis{3-(2-ethoxybenzyl)minopropanoyl}-8a-aza-8a-homoerythromycin A 3.2 mg; MS 1159

EXAMPLE 121

4",11'-O-Bis{3-(1S)-1-(4-methoxyphenyl)ethyl)aminopropanoyl}-8a-aza-8a-homoerythromycin A 3.5 mg; MS 1159

EXAMPLE 122

4",11'-O-Bis{3-(1R)-1-(4-methoxyphenyl)ethyl)aminopropanoyl}-8a-aza-8a-homoerythromycin A 3.6 mg; MS 1159

EXAMPLE 123

4",11'-O-Bis{3-(1S)-1-(4-nitrophenyl)ethyl)aminopropanoyl}-8a-aza-8a-homoerythromycin A 3.9 mg; MS 1189

EXAMPLE 124

4",11-O-Bis{3-(1R)-1-(4-nitrophenyl)ethyl)aminopropanoyl}-8a-aza-8a-homoerythromycin A 4.1 mg; MS 1189

EXAMPLE 125

4",11-O-Bis{3-(4-nitrobenzyl)aminopropanoyl}-8a-aza-8a-homoerythromycin A 4.2 mg; MS 1161

EXAMPLE 126

4",11'-O-Bis{3-(N-methyl-N-(4-nitrophenyl))aminopropanoyl}-8a-aza-8a-homoerythromycin A 4.2 mg; MS 1217

EXAMPLE 127

4",11'-O-Bis{3-(2-pyridylmethyl)aminopropanoyl}-8a-aza-8a-homoerythromycin A 3.4 mg; MS 1073

EXAMPLE 128

4",11-O-Bis{3-(2-(2-pyridyl)ethyl)aminopropanoyl}-8a-aza-8a-homoerythromycin A 3.3 mg; MS 1101

EXAMPLE 129

4",11'-O-Bis{3-(2-phenoxy-1-ethan)aminopropanoyl}-8a-aza-8a-homoerythromycin A 2.6 mg; MS 1131

The above examples 99 to 129 were obtained starting from Example 97(5 mg) and 10 equivalents of amine, following the same procedure described in Example 98.

The amounts of reagent used (i.e amine compound) have been listed in Table 2.

TABLE 2

| Example no. | Amine | Amine (mg) |
|---|---|---|
| Ex 99 | (2-pyridyl)-CH₂CH₂-NH-CH₃ | 8.4 |
| Ex 100 | 6,7-dimethoxy-1,2,3,4-tetrahydroisoquinoline | 12.0 |
| Ex 101 | (1R,2S)-2-amino-3-methoxy-1-phenylpropan-1-ol · HCl | 11.2 |
| Ex 102 | 3,5-dimethoxybenzylamine | 10.4 |

TABLE 2-continued

| Example no. | Amine | Amine (mg) |
|---|---|---|
| Ex 103 | (N-ethyl-N-(pyridin-4-ylmethyl)amine) | 8.4 |
| Ex 104 | (4-(trifluoromethoxy)benzylamine) | 11.9 |
| Ex 105 | (3-(trifluoromethoxy)benzylamine) | 11.9 |
| Ex 106 | (2-amino-1-(4-methoxyphenyl)ethanone) | 10.2 |
| Ex 107 | (3-methoxy-4-hydroxyphenethylamine) | 10.4 |
| Ex 108 | (L-phenylalaninol hydrochloride) | 9.4 |
| Ex 109 | (4-methoxybenzylamine) | 8.5 |
| Ex 110 | (3,4-dimethoxyphenethylamine) | 11.2 |
| Ex 111 | (4-(aminomethyl)pyridine) | 6.7 |
| Ex 112 | (3-(aminomethyl)pyridine) | 6.7 |
| Ex 113 | (4-methoxyphenethylamine) | 9.4 |
| Ex 114 | (3,4-dimethoxybenzylamine) | 10.4 |
| Ex 115 | (4-nitrophenethylamine) | 10.3 |
| Ex 116 | (2,4-dimethoxybenzylamine) | 10.4 |
| Ex 117 | (2-methoxybenzylamine) | 8.5 |
| Ex 118 | (benzo[d][1,3]dioxol-5-ylmethanamine) | 9.4 |
| Ex 119 | (3,4,5-trimethoxybenzylamine) | 12.2 |
| Ex 120 | (2-ethoxybenzylamine) | 9.4 |
| Ex 121 | ((R)-1-(4-methoxyphenyl)ethanamine) | 9.4 |
| Ex 122 | ((S)-1-(4-methoxyphenyl)ethanamine) | 9.4 |
| Ex 123 | (1-(4-nitrophenyl)ethanamine) | 10.3 |

TABLE 2-continued

| Example no. | Amine | Amine (mg) |
|---|---|---|
| Ex 124 | 4-nitro-α-methylbenzylamine (chiral) | 10.3 |
| Ex 125 | 4-nitrobenzylamine | 9.4 |
| Ex 126 | N-methyl-2-(4-nitrophenyl)ethylamine | 11.2 |
| Ex 127 | 2-(aminomethyl)pyridine | 6.7 |
| Ex 128 | 2-(2-aminoethyl)pyridine | 7.6 |
| Ex 129 | 2-phenoxyethylamine | 8.5 |

EXAMPLE 130

4"-O-(Propenoyl)-6-O-methyl-8a-aza-8a-homoerythromycin A 2.0 g of 6-OMe-8a-aza-8a-homoerythromycin was dissolved in 100 ml of CH$_2$Cl$_2$ at room temperature. To this solution 900 mg of NaHCO$_3$ and 280 μl of Ac$_2$O were added. Stirring over night. To this mixture 100 ml of brine and 50 ml of water were added. The organic layer was separated, washed with 50 ml brine, dried and evaporated to yield 2.1 g of the 2'-OAc-4"O-(Propenoyl)-6-O-methyl-8a-aza-8a-homoerythromycin A.

290 mg of said compound were dissolved in 10 ml toluene and the solvent was evaporated. This was performed 2 times. After that the residue was again dissolved in 15 ml toluene and stirred under argon. To this solution was added 470 μl TEA and 101 μl 3 chloropropionyl-chloride (in three portions in a period of 10 minutes). After 15 h 235 μl TEA and 50 μl of 3 chloro-propionylchloride were added. 3 h later 170 μl TEA and 25 μl of 3 chloro-propionylchloride were added.

After that 30 ml of sat. NaHCO$_3$ was added. Extraction with 3×20 ml toluene. Drying and evaporation of the solvent yielded 261 mg of the product.

This residue was dissolved in 30 ml of MeOH and stirred over night to yield after evaporation of the solvent the title compound (300 g).

MS (ES+) 817.1

EXAMPLE 131

4"-O-{3-(4-nitrophenethyl)aminopropanoyl}-6-O-methyl-8a-aza-8a-homoerythromycin A To example 130 (5 mg) dissolved in 200 μl of acetonitrile was added 5 eq of the amine 4-nitrophenethylamine hydrochloride (followed by the addition of 5 μl of DIPEA). This mixture was heated at 70° C. for 48 hours and cooled to room temperature and the scavanger resin [30 mg] (4-benzyloxybenzaldehyde polymer bound) and CH$_2$Cl$_2$ (600 μl) were added. After 2 days the resin is filtered off, washed with methanol (300 μl), CH$_2$Cl$_2$ (300 μl) and again with methanol (300 μl). The solvent was evaporated giving the title compound de

MS (ES+) 983.2

EXAMPLE 132

4"-O-{3-(N-methyl-N-[2-(2-pyridylethyl]aminopropanoyl}6-O-methyl 8a-aza-8a-homoerythromycin A 3.9 mg; MS 953

EXAMPLE 133

4"-O-{3-(6,7-dimethoxy-1,2,3,4-tetrahydroisoquinol-2-yl)propanoyl}-6-O-methyl 8a-aza-8a-homoerythromycin A 4.0 mg; MS 1010

EXAMPLE 134

4"-O-{3-(1R,2S)-2-(2-amino-3-methoxy-1-phenylpropan-1-ol-6-O-methyl)propanoyl}-8a-aza-8a-homoerythromycin A 2.9 mg; MS 998

EXAMPLE 135

4"-O-{3-(3,5-dimethoxybenzyl) aminopropanoyl}-6-O-methyl-8a-aza-8a-homoerythromycin A 3.3 mg; MS 984

EXAMPLE 136

4"-O-{3-(N-ethyl-N-(4-pyridylmethyl) aminopropanoyl}-6-O-methyl-8a-aza-8a-homoerythromycin A 3.8 mg; MS 953

EXAMPLE 137

4"-O-{3-[4-(trifluoromethoxy)phenyl]benzyl)aminopropanoyl}-6-O-methyl-8a-aza-8a-homoerythromycin A 3.9 mg; MS 1008

EXAMPLE 138

4"-O-{3-[3-(trifluoromethoxy)phenyl]benzyl)aminopropanoyl}-6-O-methyl-8a-aza-8a-homoerythromycin A 3.8 mg; MS 1008

EXAMPLE 139

4"-O-{3-(1-(4-methoxyphenyl)-1-ethanone)aminopropanoyl}-6-O-methyl-8a-aza-8a-homoerythromycin A 2.6 mg; MS 982

EXAMPLE 140

4"-O-{3-(2-methoxyphenol-4-(ethyl)aminopropanoyl}-6-O-methyl 8a-aza-8a-homoerythromycin A 3.6 mg; MS 984

EXAMPLE 141

4"-O-{(2S)-2-(3-aminopropanoyl)-3-phenylpropan-1-ol}-6-O-methyl-8a-aza-8a-homoerythromycin A 2.7 mg; MS 968

EXAMPLE 142

4"-O-{3-(4-methoxybenzyl)aminopropanoyl}-6-O-methyl 8a-aza-8a-homoerythromycin A 3.6 mg; MS 954

EXAMPLE 143

4"-O-{3-(3,4-dimethoxyphenethyl)aminopropanoyl}-6-O-methyl-8a-aza-8a-homoerythromycin A 3.8 mg; MS 998

EXAMPLE 144

4"-O-{3-(4-pyridylethyl)aminopropanoyl}-6-O-methyl-8a-aza-8a-homoerythromycin A 4.0 mg; MS 925

EXAMPLE 145

4"-O-{3-(3-pyridylethyl)aminopropanoyl}-6-O-methyl 8a-aza-8a-homoerythromycin A 4.1 mg; MS 925

EXAMPLE 146

4"-O-{3-(4-methoxyphenethyl)aminopropanoyl}-6-O-methyl-8a-aza-8a-homoerythromycin A 3.6 mg; MS 968

EXAMPLE 147

4"-O-{3-(3,4-dimethoxybenzyl)aminopropanoyl}-6-O-methyl 8a-aza-8a-homoerythromycin A 3.9 mg; MS 984

EXAMPLE 148

4"-O-{3-(4-nitrophenethyl)aminopropanoyl}-6-O-methyl 8a-aza-8a-homoerythromycin A 4.4 mg; MS 983

EXAMPLE 149

4"-O-{3-(2,4-dimethoxybenzyl)aminopropanoyl}-6-O-methyl-8a-aza-8a-homoerythromycin A 3.6 mg; MS 984

EXAMPLE 160

4"-{3-(2-methoxybenzyl)aminopropanoyl}-6-O-methyl-8a-aza-8a-homoerythromycin A 3.5 mg; MS 954

EXAMPLE 151

4"-O-{3-(1,3-benzodioxazol-5-yl-methyl)aminopropanoyl}-6-O-methyl-8a-aza-8a-homoerythromycin A 3.8 mg; MS 968

EXAMPLE 152

4"-O-{3-(3,4,5-trimethoxybenzyl)aminopropanoyl}-6-O-methyl-8a-aza-8a-homoerythromycin A 3.4 mg; MS 1014

EXAMPLE 153

4"-O-{3-(2-ethoxybenzyl)aminopropanoyl}-6-O-methyl-8a-aza-8a-homoerythromycin A 2.8 mg; MS 968

EXAMPLE 154

4"-O-{3-(1S)-1-(4-methoxyphenyl)ethyl)aminopropanoyl}-6-O-methyl-8a-aza-8a-homoerythromycin A 3.8 mg; MS 968

EXAMPLE 155

4"-O-{3-(1R)-1-(4-methoxyphenyl)ethyl)aminopropanoyl}-6-O-methyl-8a-aza-8a-homoerythromycin A 3.6 mg; MS 968

EXAMPLE 156

4"-O-{3-(1S)-1-(4-nitrophenyl)ethyl)aminopropanoyl}6-O-methyl-8a-aza-8a-homoerythromycin A 4.0 mg; MS 983

EXAMPLE 157

4"-O-{(1R)-1-(4-nitrophenyl)ethyl-2-aminopropanoyl}-6-O-methyl-8a-aza-8a-homoerytrhromycin A 3.9 mg; MS 983

EXAMPLE 158

4"-O-{3-(4-nitrobenzyl)aminopropanoyl}-6-O-methyl-8a-aza-8a-homoerythromycin A 4.0 mg; MS 979

EXAMPLE 159

4"-O-{3-(N-methyl-N-(4-nitrophenyl)aminopropanoyl}-6-O-methyl-8a-aza-8a-homoerythromycin A 4.1 mg; MS 997

EXAMPLE 160

4"-O-{3-(2-pyridylmethyl)aminopropanoyl}-6-O-methyl-8a-aza-8a-homoerythromycin A 3.5 mg; MS 925

EXAMPLE 161

4"-O-{3-(2-(2-pyridyl)ethyl)aminopropanoyl}-6-O-methyl-8a-aza-8a-homoerythromycin A 3.6 mg; MS 939

The above examples 132 to 161 were obtained starting from Example 130 (5 mg) and 5 equivalent of amine and following the same procedure described in Example 131.

The amount of reagent used (i.e. amine compound) have been listed in table 3.

TABLE 3

| Example no. | Amine | Amine (mg) |
|---|---|---|
| 132 | 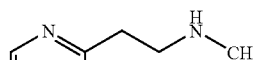 | 4.2 |
| 133 | | 6.0 |
| 134 | | 5.6 |
| 135 | | 5.2 |
| 136 | | 4.2 |
| 137 | | 5.9 |
| 138 | | 5.9 |
| 139 | | 5.1 |
| 140 | | 5.2 |
| 141 | | 4.7 |
| 142 | | 4.3 |

TABLE 3-continued

| Example no. | Amine | Amine (mg) |
|---|---|---|
| 143 | 3,4-dimethoxyphenethylamine | 5.6 |
| 144 | 4-(aminomethyl)pyridine | 3.4 |
| 145 | 3-(aminomethyl)pyridine | 3.4 |
| 146 | 4-methoxyphenethylamine | 4.7 |
| 147 | 3,4-dimethoxybenzylamine | 5.2 |
| 148 | 4-nitrophenethylamine | 5.1 |
| 149 | 2,4-dimethoxybenzylamine | 5.2 |
| 150 | 2-methoxybenzylamine | 4.3 |
| 151 | piperonylamine (3,4-methylenedioxybenzylamine) | 4.7 |
| 152 | 3,4,5-trimethoxybenzylamine | 6.1 |
| 153 | 2-ethoxybenzylamine | 4.7 |
| 154 | (R)-1-(4-methoxyphenyl)ethylamine | 4.7 |
| 155 | (S)-1-(4-methoxyphenyl)ethylamine | 4.7 |
| 156 | (R)-1-(4-nitrophenyl)ethylamine | 5.2 |
| 157 | (S)-1-(4-nitrophenyl)ethylamine | 5.2 |
| 158 | 4-nitrobenzylamine HCl | 4.7 |
| 159 | N-methyl-4-nitrophenethylamine | 5.6 |
| 160 | 2-(aminomethyl)pyridine | 3.4 |
| 161 | 2-(2-aminoethyl)pyridine | 3.8 |

PHARMACY EXAMPLES

| Tablets | mg/tab |
|---|---|
| Active ingredient | 320 |
| Lactose | 150 |
| Ethyl cellulose | 20 |
| Sodium lauryl sulphate | 7 |
| Magnesium stearate | 3 |
| Tablet core | 500 |

The active ingredient and the lactose are blended together and then granulated using water as granulating fluid. The dried granules are blended with ethyl cellulose, sodium lauryl sulphate and magnesium stearate and the tablet core formed using an appropriate punch. The tablet may be coated using conventional technique and coatings.

Injection

The sterile vials were filled with the sterile active ingredient (500 mg). Purge the vial head space with sterile nitrogen; close the vials using rubber and metal overseals. The product may be constituted by dissolving in water for injection (10 ml) or other suitable sterile vehicle for injection shortly before administration.

Activity Data

The value of MIC (microbial inhibition concentration), obtained according to NCCLS (National Committee for Clinical Laboratory Standards), of the preferred compounds of the invention against erythromycin susceptible *Streptococcus pneumoniae* and *Streptococcus pyogenes* are less then or equal to 1 ug/ml.

In particular Ex 1, Ex 2, Ex 4, Ex 37 and Ex 25 showed MIC<=0.01 and <=2 ug/ml against erythromycin susceptible and resistant *Streptococcus pneumoniae* strains, respectively.

The compounds of the invention are also essentially non-toxic at therapeutically useful dose levels.

The invention claimed is:

1. A compound of formula (I)

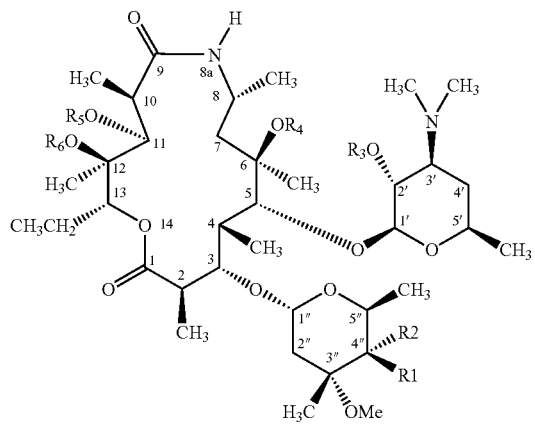

(I)

wherein
R₁ is hydrogen;
R₂ is OC(O)XR₇ or OC(O)NHXR₇;
R₃ is hydrogen;
R₄ is XR₇;
R₅ is XR₇, C(O)XR₇ or C(O)NHXR₇;
R₆ is hydrogen;
or R₅ and R₆ taken together with the intervening atoms form a cyclic carbonate having the following structure

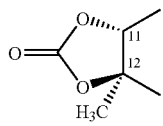

X is $C_{1-6}$ alkylene (optionally substituted by $NR_8R_9$), $C_{3-6}$ alkenyl (optionally substituted by $NR_8R_9$), or the group $(CH_2)pY(CH_2)q$ wherein Y is O or $NR_8$ and the sum of p and q is an integer from 2 to 6; and R₇ is hydrogen, phenyl (optionally substituted by one or two groups selected from halogen, nitro, trifluoromethoxy, cyano, and 5 or 6-membered heteroaryl group), pyridyl, 3-quinolyl, 4-quinolyl, benzoxazolyl, 1,3 benzothiazolyl, 1,2,3,4-tetra hydro-quinolyl, cyclopropyl, benzimidazolyl, isoquinolyl, naphthyl or furanyl;

R₈ and R₉ independently represent hydrogen or $C_{1-4}$ alkyl optionally substituted by 1 or 2 groups selected from:
phenyl, optionally substituted by $C_{1-4}$ alkoxy or nitro,
5-membered heteroaryl containing 1 or 2 heteroatoms selected from oxygen, sulphur and nitrogen,
hydroxy,
oxo, and
carboxy,
or
R₈ and R₉ independently represent a phenyl optionally substituted by one or two $C_{14}$ alkyl groups, or a nitrogen protecting group; or a pharmaceutically acceptable salt thereof.

2. A compound as claimed in claim 1 in which
R₂ is $OC(O)X_aR_7$ or $OC(O)X_bR_{7a}$;
$X_a$ is $C_{1-6}$ alkylene substituted by $NR_8R_9$, $C_{3-6}$ alkenyl (optionally substituted by $NR_8R_9$), or the group $(CH_2)pY(CH_2)q$ wherein Y is O or NR8, and the sum of p and q is an integer from 2 to 6;
$X_b$ is $C_{1-6}$ alkylene; and
$R_{7a}$ is phenyl (which is substituted by one or two groups selected from halogen, nitro, trifluoromethoxy, cyano, or 5 or 6-membered heteroaryl group), pyridyl, 3-quinolyl, 4-quinolyl, benzoxazolyl, 1,3 benzothiazolyl, 1,2,3 4-tetra hydro-quinolyl, cyclopropyl, benzimidazolyl, isoquinolyl, naphthyl or furanyl; or a pharmaceutically acceptable salt thereof.

3. A compound selected from
4"-O-[3-(3-quinolyl)-2-ethenylcarbonyl]-6-O-methyl-8a-aza-8a-homoerythromycin A;
4"-O-(4-nitrophenylacetyl)-6-O-methyl-8a-aza-8a-homoerythromycin A;
4"-O-[3-(3-quinolyl)-2-ethenylcarbonyl]-8a-aza-8a-homoerythromycin A;
4"-O-[3-(1,2,3 ,4-tetrahydro-3-quinolyl)-ethyl-carbonyl]-6-O-methyl-8a-aza-8a-homoerythromycin A;
4"-O-(4-(3-quinolyl)butanoyl)-6-O-methyl-8a-aza-8a-homoerythromycin A;
4"-O-(5-(3-quinolyl)-pentanoyl)-6-O-methyl-8a-aza-8a-homoerythromycin A;
4"-O-(5-(3-quinolyl)-4-pentenoyl)-6-O-methyl-8a-aza-8a-homoerythromycin A;
4"-O-[3-(3-quinolyl)-4-butenylcarbonyl]-8 a-aza-8a-homoerythromycin A;
4"-O-(4-(3-quinolyl)-3-butenoyl)-6-O-methyl-8 a-aza-8a-homoerythromycin A;
4"-O-(3-quinolyl)propenoyl-6-O-ethyl-8a-aza-8a-homoerythromycin A;
4"-O-(4-nitrophenyl)acetyl-6-O-ethyl-8a-aza-8a-homoerythromycin A; and
4"-O-(p-Nitrophenylcarbamoyl)-6-O-methyl-8a-aza-8 a-homoerythromycin A; or a pharmaceutically acceptable salt thereof.

4. Preparation of a compound of claim 1 comprising reacting a compound of formula (Ia)

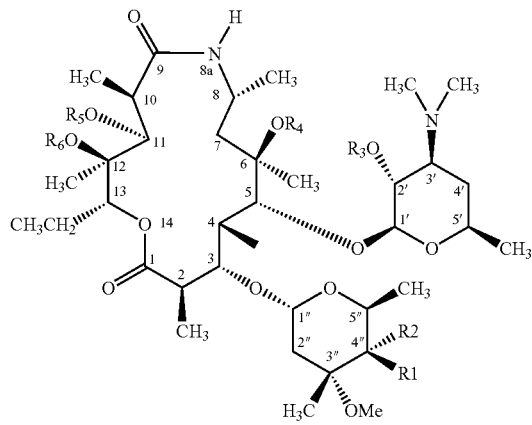

(Ia)

wherein $R_2$ is hydroxyl and $R_1$, $R_3$, $R_4$, $R_5$, and $R_6$ are as defined in claim 1 with:

(a) an activated derivative of $HOCOXR_7$, wherein X and $R_7$ are as defined in claim 1, to obtain compounds of formula (I) in which $R_2$ is a $OC(O)XR_7$ group; or an isocyanate derivative of $R_7XNCO$ (III), wherein X and $R_7$ are as defined in claim 1, to obtain compounds of formula (I) in which $R_2$ is a $OC(O)NHXR_7$ group.

5. A pharmaceutical composition comprising a compound according to claim 1, or a pharmaceutically acceptable salt thereof, in admixture with one or more pharmaceutically acceptable carriers or excipients.

6. A method for the treatment of the human or non human animal body to combat bacterial infection comprising administration of an effective amount of a compound, or pharmaceutically acceptable salt thereof, according to claim 1 to said human or non human animal body.

* * * * *